(12) United States Patent  
Redelmeier et al.

(10) Patent No.: US 9,295,735 B2  
(45) Date of Patent: Mar. 29, 2016

(54) LIPOSOMAL COMPOSITION FOR CONVECTION-ENHANCED DELIVERY TO THE CENTRAL NERVOUS CENTRE

(75) Inventors: Thomas Redelmeier, Vancouver (CA); Matthias Luz, Mannheim (DE)

(73) Assignee: MEDGENESIS THERAPEUTIX, INC., Victoria (CA)

( * ) Notice: Subject to any disclaimer, the term of this patent is extended or adjusted under 35 U.S.C. 154(b) by 682 days.

(21) Appl. No.: 13/130,525

(22) PCT Filed: Nov. 23, 2009

(86) PCT No.: PCT/CA2009/001708  
§ 371 (c)(1),  
(2), (4) Date: Jul. 26, 2011

(87) PCT Pub. No.: WO2010/057317  
PCT Pub. Date: May 27, 2010

(65) Prior Publication Data  
US 2011/0274625 A1 Nov. 10, 2011

Related U.S. Application Data

(60) Provisional application No. 61/117,076, filed on Nov. 21, 2008.

(51) Int. Cl.  
*A61K 9/127* (2006.01)  
*A61K 49/00* (2006.01)  
(Continued)

(52) U.S. Cl.  
CPC ............ *A61K 49/0084* (2013.01); *A61K 9/0019* (2013.01); *A61K 9/127* (2013.01);  
(Continued)

(58) Field of Classification Search  
CPC ...................................... A61K 9/127  
USPC ........................................................ 424/450  
See application file for complete search history.

(56) References Cited

U.S. PATENT DOCUMENTS 5,281,693 A * 1/1994 Jackson et al. ................. 530/324  
2007/0110798 A1 * 5/2007 Drummond et al. .......... 424/450  
(Continued)

FOREIGN PATENT DOCUMENTS

WO           99/52505    * 10/1999  
WO    WO 99/52505 A2   10/1999  
(Continued)

OTHER PUBLICATIONS

Saito et al, Experimental Neurology, vol. 196, pp. 381-389, 2005.*  
(Continued)

*Primary Examiner* — Gollamudi Kishore  
(74) *Attorney, Agent, or Firm* — Arnold & Porter LLP; Todd A. Lorenz

(57) ABSTRACT

Convection-enhanced delivery (CED) is used as a method to deliver a direct infusion of therapeutic agents to the central nervous center thus circumventing the blood-blood barrier. A non-PEGylated liposomal composition comprising at least one saturated neutral phospholipid and at least one saturated anionic phospholipid and a therapeutic or diagnostic agent encapsulated therein is used to overcome toxicity associated with high peak drug concentration delivered locally CED as well as to increase tissue distribution volume for an improved sustained drug release. In one embodiment, the liposome composition comprises a molar ratio of DSPC:DSPG:CHOL of 7:2:1 and the therapeutic or diagnostic agent is selected from topotecan, conotoxin, gadodiamide or rhodamine, and is used in the treatment of epilepsy.

12 Claims, 9 Drawing Sheets

Topotecan Release in Serum: Effect of Drug:Lipid Ratio

(51) Int. Cl.
A61K 9/00 (2006.01)
A61K 31/4745 (2006.01)
A61M 25/00 (2006.01)

(52) U.S. Cl.
CPC ......... *A61K31/4745* (2013.01); *A61K 49/0023* (2013.01); *A61K 49/0041* (2013.01); *A61M 25/007* (2013.01); *A61M 2025/0042* (2013.01)

(56) References Cited

U.S. PATENT DOCUMENTS

| | | | | |
|---|---|---|---|---|
| 2007/0254019 | A1* | 11/2007 | Zamboni et al. | 424/450 |
| 2009/0209937 | A1* | 8/2009 | Rogawski et al. | 604/503 |
| 2010/0015213 | A1* | 1/2010 | Golomb et al. | 424/450 |

FOREIGN PATENT DOCUMENTS

| | | | |
|---|---|---|---|
| WO | WO 02/089771 A2 | 11/2002 | |
| WO | 03/041681 | * | 5/2003 |
| WO | WO 03/041681 A2 | 5/2003 | |
| WO | 2004/087115 | * | 10/2004 |
| WO | WO 2004/087115 A2 | 10/2004 | |
| WO | WO 2005/079185 A2 | 9/2005 | |
| WO | WO 2006/127962 A2 | 11/2006 | |
| WO | WO 2007/127839 A2 | 4/2007 | |
| WO | WO 2008/100930 A2 | 8/2008 | |

OTHER PUBLICATIONS

Bobo RH, Laske DW, Akbasak A, et al., Convection-enhanced delivery of macromolecules in the brain. Proc. Natl. Acad. Sci. USA 91:2076-80 1994.

Bruce, et al., Intracerebral clysis in a rat glioma model, Neurosurgery 46. 683-691, 2000.

Chen, MY, et al., Variables affecting convection-enhanced delivery to the striatum: a systematic examination of rate of infusion, cannula size, infusate concentration, and tissue—cannula sealing time J. Neurosurg. 90:315-20, 1999.

Croteau D, Walbridge S, Morrison PF, Butman JA, Vortmeyer AO, et al. Real-time in vivo imaging of the convective distribution of a low-molecular-weight tracer. J Neurosurg 102:90-97, 2005.

Degen, et al., Safety and efficacy of convection-enhanced delivery of gemcitabine or carboplatin in a malignant glioma model in rats, J. Neurosurg. 99:893-898, Nov. 2003.

Grahn, AY, et al., "Non-PEGylated Lipsomes for Convection-enhanced Delivery of Topotecan and Gadodiamide in Malignant Glioma: Initial Experience," Journal of Neurooncolgy, May 24, 2009, vol. 95, pp. 185-197.

Ishida and Kiwada, Accelerated blood clearance (ABC) phenomenon upon repeated injection of PEGylated liposomes, Int. J. Pharm. 354:56-62. Nov. 9, 2007.

Kaiser MG, Parsa AT, Fine RL, Hall JS, Chakrabarti I, et al. Tissue distribution and antitumor activity of topotecan delivered by intracerebral clysis in a rat glioma model. Neurosurg 47: 1391-1398, 2000.

Lonser RR, Walbridge S, Garmestani K, Butman JA, Walters HA, et al. Successful and safe perfusion of the primate brainstem: in vivo magnetic resonance imaging of macromolecular distribution during infusion. J Neurosurg 97:905-913, 2002.

Moghimi, et. al., Methylation of the phospate oxygen moiety of phospholipid-methoxy (polyethyleme glycol) conjugated prevents PEGylated liposome-mediated complement activation and anaphylatoxin production, FASEB Journal 20:E2057-E2067, Dec. 2006.

Moog R, Burger AM, Brandi M, et al. Change in pharmacokinetics and pharmacodynamic behavior of gercitabine in human tumor xenografts upon entrapment in vesicular phospholipid gels. Cancer Chemother Pharmacol 49:356-366, 2002.

Noble, et al., Novel nanoliposomal CPT-11 infusted by convection-enhanced delivery in intracranial tumors: pharmacology and efficacy, Cancer res. 66(5):2801-2806, Mar. 1, 2006.

Saito R, Krauze MT, Noble CO, Drummond DC, Kirpotin DB, et al. Convection-enhanced delivery of Ls-TPT enables an effective, continuous, low dose chemotherapy against malignant glioma xenograft model. Neuro—Oncol 8:205-214, 2006.

Saito R, et. al., Tissue affinity of the infusate affects the distribution volume during convection-enhanced delivery into rodent brains: implications for local drug delivery, Jounral of Neuroscience Methods 154, 225-232, 2006.

Szebeni, et al., Animal models of complement-mediated hypersensitivity reactions to liposomes and other lipid-based nanoparticle, J. Liposome Res. 17:107-117, 2007.

Woodle, et. al., Sterically Stabilized Liposomes: Reduction in Electrophoretic Mobility but not Electrostatic Surface Potential, Biophys. J. 61, 902-910, Apr. 1992.

* cited by examiner

Topotecan Release in Serum: Effect of Lipid Composition
(D:L 0.1:1)

Topotecan Release in Serum: Effect of Drug:Lipid Ratio
(450 mM Ammonium Sulfate)

Topotecan Release in Serum: Effect of Drug Concentration
(DSPC / Chol / PEG2000-DSPE / 250 mM AmSO4, 0.1 D:L)

Topotecan Release in Serum: Effect of Drug Concentration
(DSPC / Chol 450 mM AmSO4, 0.1 D:L)

Topotecan Release in Serum: Effect of
Drug Concentration and Lipid Composition
(DSPC / Chol 450 mM AmSO4, 0.1 D:L)

Topotecan Release in Serum: Effect of
Drug Concentration
(DSPC/DSPG/Chol 450 mM AmSO4, 0.3 D:L)

US 9,295,735 B2

LIPOSOMAL COMPOSITION FOR CONVECTION-ENHANCED DELIVERY TO THE CENTRAL NERVOUS CENTRE

FIELD OF THE INVENTION

The present invention relates to liposomal formulations that are deliverable by convection-enhanced delivery and useful for the treatment of central nervous system disorders.

BACKGROUND OF THE INVENTION

For patients with brain tumors, systemic delivery of therapeutics is usually associated with systemic side effects while achieving only marginal therapeutic concentrations in the central nervous system (CNS), and thus the efficacy of systemic treatment is limited. The observed lack of efficacy is primarily due to poor penetration of therapeutic agents across the blood-brain barrier. Although the blood-brain barrier may be disrupted at the core of the tumor allowing systemically-delivered chemotherapy agents access to the mostly inactive center of the tumor, the barrier typically remains intact at the growing tumor margin where the agent is needed most.

One approach to circumventing the blood brain barrier is direct infusion of therapeutic agents into the CNS. However, agents infused directly into the brain distribute poorly by diffusion. High concentration gradients are required to move even small molecule drugs millimeters from the infusion site, and such concentrations are often neurotoxic. A developing strategy to overcome this problem is a direct intracerebral infusion approach called convection-enhanced delivery (CED). CED employs positive pressure to generate a local pressure gradient for distributing agents, including therapeutic macromolecules, in the extracellular space. (Bobo, R. H., et al. (1994) Proc. Natl. Acad. Sci. USA 91:2076-80; Chen, M. Y., et al. (1999) J. Neurosurg. 90:315 20). CED provides reproducible distribution within a given target tissue and can produce homogeneous drug concentrations throughout the volume of distribution ($V_d$) (Croteau et al., 2005; Lonser et al., 2002).

Chemotherapeutic agents delivered locally by CED have produced favorable therapeutic outcomes (Bruce et al., 2000; Degen et al., 2003; Kaiser et al. 2000). However, most cytotoxic agents delivered directly to the nervous system have the capacity to damage healthy cells. Accordingly, good candidates for CED administration into brain tumors must have the highest possible therapeutic index against tumor cells in comparison with healthy neuronal cells. While liposomal drug delivery offers potential for avoiding the high peak drug concentrations that are often associated with pronounced toxicity, and preclinical studies of liposome-encapsulated camptothecin drugs given via CED have shown some improvement in the sustained release of the drug (Moog et al, 2002; Saito et al, 2006; Nobel et al, 2006), the use of PEGylated liposomes was deemed essential to mask tissue binding site interactions and thereby increase tissue distribution volume. (Saito et al, 2006).

Despite the success of PEGylation in overcoming liposome/tissue interactions, it has recently been demonstrated that PEGylated liposomes may generate unwanted and potentially life-threatening immune responses (Szebeni et al. (2007) J. Liposome Res. 17:107-117; Ishida and Kiwada (2008) Int. J. Pharm. 354:56-62 Epub Nov. 9, 2007). In addition to accelerated blood clearance when administered into the same subject twice, PEGylated liposomes may cause non-IgE-mediated hypersensitivity reactions, which include symptoms of cardiopulmonary distress (e.g., dyspnea, tachypnea, tachycardia, chest pain, hypertension, and hypotension) (Ishida and Kiwada (2008), supra; Moghimi et al. (2006) FASEB J. 20:2591-3 Epub Oct. 25, 2006).

What is needed, therefore, is an improved liposomal drug formulation for convection-enhanced delivery that provides increased tissue distribution volume, but avoids the problematic immunogencity associated with PEGylation.

SUMMARY OF THE INVENTION

The present inventors have surprisingly discovered that liposomes can be highly convective in tissues of the central nervous system when an anionic lipid component is employed in the formulation in lieu of PEGylation, as described and claimed herein. Moreover, the subject formulations exhibit pharmacokinetic profiles comparable to PEGylated formulations employed in the art while avoiding the problematic immunogencity associated with PEGylation. Accordingly, provided herein are improved compositions and methods of administering therapeutic drugs to discrete tissue(s) of the central nervous system (CNS), e.g., a localized CNS tumor, via convection-enhanced delivery of anionic liposome formulations.

In one aspect, described herein are methods for treating a CNS disorder, e.g., a disorder associated with the death and/or dysfunction of a particular neuronal population in the CNS. The methods involve administering a therapeutically effective amount of a pharmaceutical composition to a patient having a CNS disorder, wherein the pharmaceutical composition is locally delivered to the particular neuronal population by convection-enhanced delivery, and wherein the pharmaceutical composition comprises at least one therapeutic agent encapsulated in non-PEGylated liposomes comprising a mixture of a neutral saturated phospholipid and at least one anionic saturated lipid, and wherein the convection-enhanced delivery of the pharmaceutical composition treats a patient having a CNS disorder.

Therapeutic agents finding advantageous use in the subject invention include, e.g., antineoplastic agents, radioiodinated compounds, toxins (including protein toxins), cytotoxic agents including cytostatic or cytolytic drugs, genetic and viral vectors, vaccines, synthetic vectors, growth factors, neurotrophic factors, antivirals, antibiotics, neurotransmitters, cytokines, enzymes and agents for targeted lesioning of specific sites.

CNS disorders that may be treated by the compositions and methods provided herein include, e.g., cancer, infection, head trauma, spinal cord injury, multiple sclerosis, dementia with Lewy bodies, ALS, lysosomal storage disorders, psychiatric disorders, neurodegenerative disorders, stroke, epilepsy, and other acute and chronic disorders of the CNS.

In one embodiment, provided herein are methods for inhibiting the growth of a CNS tumor, reducing a CNS tumor, killing one or more CNS tumor cells, and/or treating a patient having a CNS tumor. The methods involve administering a therapeutically effective amount of a pharmaceutical composition to a patient having a CNS tumor, wherein the pharmaceutical composition is locally delivered to the CNS tumor by convection-enhanced delivery, and wherein the pharmaceutical composition comprises at least one cytotoxic agent encapsulated in non-PEGylated liposomes comprising a mixture of a neutral saturated phospholipid and at least one anionic saturated lipid, and wherein the convection-enhanced delivery of the pharmaceutical composition inhibits the growth of a CNS tumor, reduces a CNS tumor, kills one or more of the CNS tumor cells and/or treats a patient having a CNS tumor.

In another embodiment, provided herein are methods for inhibiting or reducing the number or duration of seizures in a patient having epilepsy. The methods involve administering a therapeutically effective amount of a pharmaceutical composition to a patient having epilepsy, wherein the pharmaceutical composition is locally delivered to an aggregate of CNS neurons exhibiting abnormal or excessive hypersynchronous discharges by convection-enhanced delivery, and wherein the pharmaceutical composition comprises at least one therapeutic agent encapsulated in non-PEGylated liposomes comprising a mixture of a neutral saturated phospholipid and at least one anionic saturated lipid, and wherein the convection-enhanced delivery of the pharmaceutical composition inhibits or reduces the number or duration of seizures in a patient having epilepsy. In one embodiment, the therapeutic agent is a toxin, e.g., a peptide toxin. In one embodiment, the peptide toxin is a ω-conotoxin, e.g., ω-conotoxin MVIIA or ω-conotoxin, GVIA. In another embodiment, the toxin is a botulinum toxin, e.g., a botulinum toxin serotype A such as BOTOX® or DYSPORT®, a botulinum toxin serotype B such as MYOBLOC®, etc. In another embodiment, the toxin is μ-conotoxin or α-conantokin peptide.

In one embodiment, the pharmaceutical composition further comprises at least one diagnostic agent (sometimes referred to herein as a "tracing agent" or "tracer") encapsulated in similar non-PEGylated anionic liposomes, which allows for visualization of the distribution of the therapeutic agent during and after CED. In preferred embodiments, the non-PEGylated liposomes encapsulating the diagnostic agent are composed of the same lipids as the non-PEGylated liposomes encapsulating the therapeutic agent. Accordingly, in one embodiment, methods described herein further comprise the step of detecting the diagnostic agent.

As described herein, the non-PEGylated liposomes may contain a therapeutic drug. In one embodiment, the therapeutic drug is an insoluble therapeutic drug. In another embodiment, the therapeutic drug is a topoisomerase I inhibitor (e.g., a camptothecin and derivatives thereof), which includes but is not limited to topoisomerase I/II inhibitors. For example, in one embodiment, the therapeutic drug is a camptothecin derivative selected from the group consisting of 9-aminocamptothecin, 7-ethylcamptothecin, 10-hydroxycamptothecin, 9-nitrocamptothecin, 10,11-methlyenedioxycamptothecin, 9-amino-10,11-methylenedioxycamptothecin 9-chloro-10,11-methylenedioxycamptothecin, irinotecan, topotecan, 7-(4-methylpiperazinomethylene)-10,11-ethylenedioxy-20(S)-camptothecin, 7-(4-methylpiperazinomethylene)-10,11-methylenedioxy-20(S)-camptothecin and 7-(2-(N-isopropylamino)ethyl)-(20S)-camptothecin. In another embodiment, the camptothecin derivative is selected from the group consisting of irinotecan, topotecan, (7-(4-methylpiperazinomethylene)-10,11-ethylenedioxy-20(S)-camptothecin, 7-(4-methylpiperazinomethylene)-10,11-methylenedioxy-20(S)-camptothecin or 7-(2-(N-isopropylamino)ethyl)-(20S)-camptothecin. In another embodiment, the camptothecin is topotecan.

In another embodiment, the topoisomerase inhibitor is a topoisomerase I/II inhibitor, such as 6-[[2-(dimethylamino)-ethyl]amino]-3-hydroxy-7H-indeno[2,1-c]quinolin-7-one dihydrochloride, azotoxin or 3-methoxy-11H-pyrido[3',4'-4,5]pyrrolo[3,2-c]quinoline-1,4-dione.

In another embodiment, the therapeutic drug is a toxin, e.g., a protein toxin, e.g., ω-conotoxin, (e.g., ω-conotoxin MVIIA or ω-conotoxin, GVIA), a botulinum toxin (e.g., a botulinum toxin serotype A such as BOTOX® or DYSPORT®, a botulinum toxin serotype B such as MYOBLOC®) μ-conotoxin, α-conantokin peptide, etc.

In one embodiment, the initial drug concentration is at least about 100 ug/mL, preferably at least about 200 ug/mL, and more preferably at least about 300 ug/mL. In another embodiment, the initial drug concentration is about 2 mg/ml to about 5 mg/ml. In one embodiment, the therapeutic drug and/or diagnostic agent to lipid ratio is from about 0.1 to about 0.5. In another embodiment, the therapeutic drug and/or diagnostic agent to lipid ratio is about 0.1. In another embodiment, the therapeutic drug and/or diagnostic agent to lipid ratio is about 0.3. In another embodiment, the therapeutic drug and/or diagnostic agent to lipid ratio is about 0.5.

In one aspect, the non-PEGylated liposome contains a diagnostic agent. In one embodiment, the diagnostic agent is an MRI magnet. In another embodiment, the diagnostic agent is gadolinium chelate. In another embodiment, the diagnostic agent is selected from the group consisting of gadodiamide and rhodamine. In another embodiment, the diagnostic agent is gadodiamide.

The methods described herein comprise convection-enhanced delivery of a liposomal formulation comprising at least one therapeutic agent and/or at least one diagnostic agent encapsulated in non-PEGylated liposomes composed of a mixture of at least one neutral saturated phospholipid and at least one anionic saturated phospholipid. In one embodiment, the neutral saturated phospholipid is selected from the group consisting of derivatives of phosphatidylcholine and mixtures thereof, for example dipalmitoylphosphatidylcholine (DPPC), distearoylphosphatidylcholine (DSPC), dimyristoylphosphatidylcholine (DMPC), and mixtures thereof. Longer chain saturated lipids, e.g., C20 and C22, may also be used. In one embodiment, the anionic saturated phospholipid is selected from a group consisting of derivatives of phosphatidylglycerol (e.g., distearoylphosphatidylglycerol (DSPG)), dipalmitoyl phosphatidyl glycerol (DPPG), phosphatidylserine, phosphatidylinositol, phosphatidic acid and mixtures thereof.

The liposomal formulations described herein may also contain other lipid components such as sterols and derivatives (for example cholesterol (CHOL)) or sphingolipids (for example sphingomyelins and glycosphingolipids, in particular gangliosides). In preferred embodiments, the liposomal formulations will consist essentially of or consist of at least one neutral saturated phospholipid, at least one anionic saturated phospholipid and a stabilizer such as, e.g., cholesterol.

In one embodiment, the non-PEGylated liposome is composed of a combination of distearoylphosphatidylcholine (DSPC) and distearoylphosphatidylglycerol (DSPG). In one embodiment, the non-PEGylated liposome comprises about 10 to about 95 mole percent DSPC. In one embodiment, the non-PEGylated liposome comprises about 5 to about 90 mole percent DSPG. In one embodiment, the non-PEGylated liposome further comprises cholesterol (CHOL), e.g., about 5 to about 45 mole percent cholesterol. In a preferred embodiment, the liposome comprises or consists essentially of about 60 to about 90 mole percent DSPC, about 5 to about 10 mole percent cholesterol, and about 5 to about 30 mole percent DSPG. In a preferred embodiment, the non-PEGylated liposome comprises or consists essentially of DSPC, DSPG, and CHOL at a 7:2:1 molar ratio. In another embodiment, the non-PEGylated liposome comprises or consists essentially of DSPC, DSPG and CHOL at a 6:2:2 molar ratio. In another embodiment, the non-PEGylated liposome comprises or consists essentially of DSPC, DSPG and CHOL at a 5:2:3 molar ratio.

In one embodiment, convection-enhanced delivery (CED) of non-PEGylated liposomal formulations as described herein provides increased tissue distribution, decreased toxicity and increased in vivo half-life of the therapeutic drug as compared to the respective tissue distribution, toxicity, and in vivo half-life of the freely administered therapeutic drug.

In one aspect, the invention provides a cannula comprising a liposomal formulation described herein, e.g., a liposomal formulation comprising at least one therapeutic agent encapsulated in non-PEGylated liposomes composed of a mixture of at least one neutral saturated phospholipid and at least one anionic saturated phospholipid, and wherein the formulation may be delivered by convection-enhanced delivery (CED). In another embodiment, the cannula further comprises a liposomal formulation comprising a diagnostic agent encapsulated in non-PEGylated liposomes composed of a mixture of at least one neutral saturated phospholipid and at least one anionic saturated phospholipid, and wherein the formulation may be delivered by CED. In another embodiment, the cannula comprises a liposomal formulation comprising a first liposome containing a therapeutic drug and a second liposome containing a diagnostic agent, wherein neither the first nor second liposome are PEGylated, wherein the first and second lipsomes are composed of a mixture of at least one neutral saturated phospholipid and at least one anionic saturated phospholipid, and wherein the formulation may be delivered by convection-enhanced delivery (CED). The cannula is compatible with convection-enhanced delivery to the CNS. In one embodiment, the cannula is a reflux-free step-design cannula.

In one aspect, the invention provides methods for producing the liposomal formulations described herein. In one aspect, the invention provides methods for producing a medicament useful for the treatment of a patient having cancer of the CNS, which medicament comprises a liposomal formulation described herein. In one embodiment, the method comprises entrapping the therapeutic drug or diagnostic agent within the liposomes by remote loading, for example, via an ammonium sulfate gradient.

Further objects, features and advantages of the apparatuses and methods described herein will become apparent from the following detailed description taken in conjunction with the accompanying figures showing illustrative embodiments of the invention.

DETAILED DESCRIPTION

Definitions

Figure 1A:
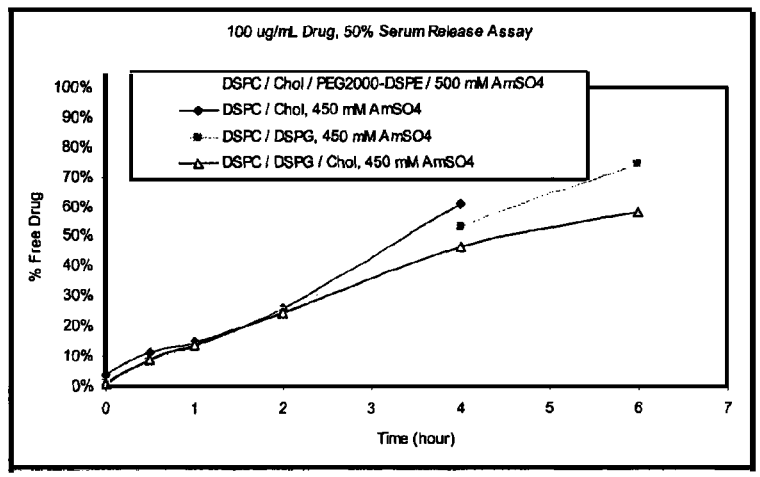
FIGS. 1A-1F compare the effect of lipid composition, drug concentration and drug:lipid ratio on the release characteristics of topotecan from pegylated and non-pegylated liposomal formulations.
Figure 1B:
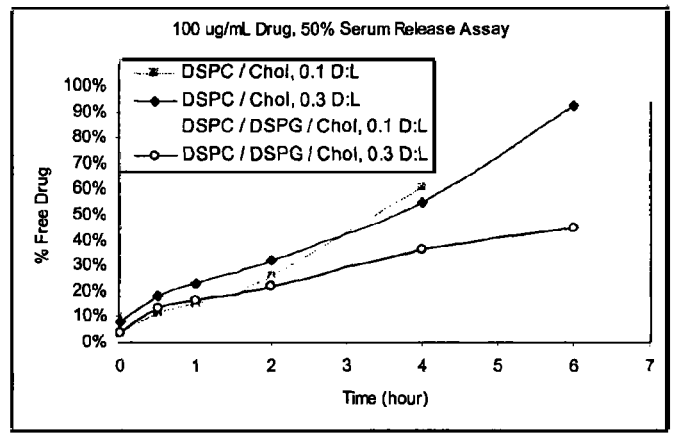
Figure 1C:
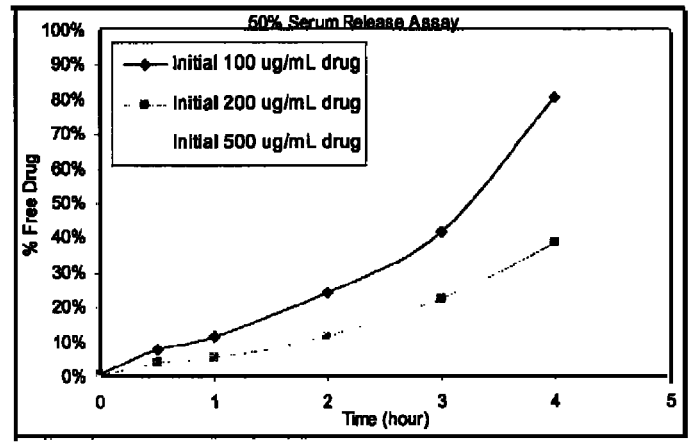
Figure 1D:
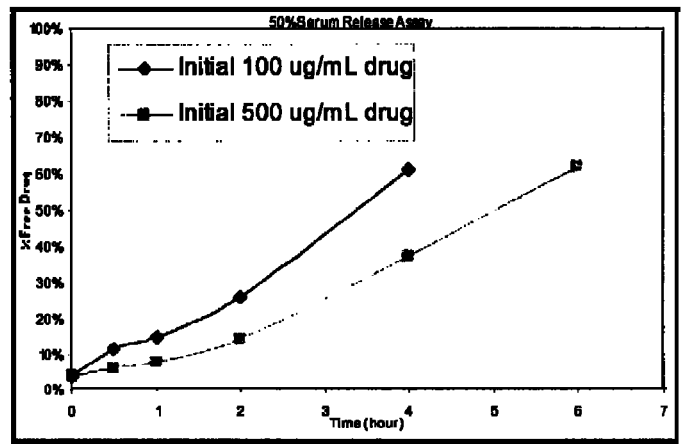
Figure 1E:
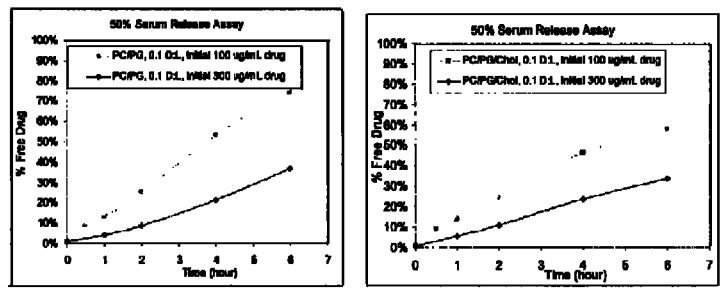
Figure 1F:
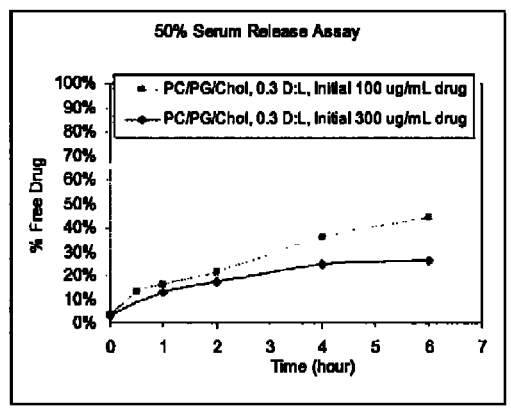

As used herein, "liposome" refers to a lipid bilayer membrane containing an entrapped aqueous volume. Liposomes may be unilamellar vesicles having a single membrane bilayer or multilamellar vesicles having multiple membrane bilayers separated from each other by an aqueous layer. Generally, the liposomal bilayer is composed of two lipid monolayers having a hydrophobic "tail" region and a hydrophilic "head" region. The structure of the membrane bilayer is such that the hydrophobic (non-polar) "tails" of the lipid monolayers orient toward the center of the bilayer while the hydrophilic (polar) "heads" orient toward either the entrapped aqueous volume or the extraliposomal aqueous environment. In one embodiment, a liposome of the invention includes a targeting moiety, e.g., an antibody or other ligand.

"Liposomal formulations" are understood to be those in which part or all of the therapeutic drug and/or diagnostic agent is encapsulated inside the liposomes. "Consisting essentially of" as used herein in reference to liposomal formulations refers to liposomes having the recited lipid components only, and no additional lipid components.

"Phospholipid" is understood to mean an amphiphile derivative of glycerol in which one of its hydroxyl groups is esterified with phosphoric acid and the other two hydroxyls are esterified with long-chain fatty acids, which may be equal or different from each other.

A saturated phospholipid will be that whose fatty acids only have simple (not multiple) covalent carbon-carbon bonds.

A neutral phospholipid will generally be one in which another phosphoric acid hydroxyl is esterified by an alcohol substituted by a polar group (usually hydroxyl or amine) and whose net charge is zero at physiological pH.

An anionic phospholipid will generally be one in which another phosphoric acid hydroxyl is esterified by an alcohol substituted by a polar group and whose net charge is negative at physiological pH.

The meaning of the expression "charged saturated phospholipid", as well as including charged saturated phospholipids, also includes other amphiphile compounds whose net charge is different from zero. Such amphiphile compounds include, but are not limited to, long chain hydrocarbonate derivatives, substituted by a polar group (for example amine) and derivatives of fatty acids.

As used herein, "active agent" or "therapeutic agent" refers to any molecule that may be delivered to CNS target tissue in the form of a high molecular weight neurotherapeutic, and when so delivered, effects a desirable response in the target CNS tissue. Therapeutic agents include but are not limited to antineoplastic agents, radioiodinated compounds, toxins (including protein toxins), cytotoxic agents including cytostatic or cytolytic drugs, genetic and viral vectors, vaccines, synthetic vectors, growth factors, neurotrophic factors, antivirals, antibiotics, neurotransmitters, cytokines, enzymes and agents for targeted lesioning of specific sites. Therapeutic agents include, but are not limited to, nucleic acids, including nucleic acid analogs, proteins, including antibodies, and small molecule chemical compositions. Active agents include agents that exhibit toxicity and unwanted effects when administered systemically.

As used herein, a "CNS disorder" refers to a disorder of the central nervous system of a subject. The disorder may be associated with the death and/or dysfunction of a particular neuronal population in the CNS. The disorder may be associated with the aberrant growth of cells within the CNS. The aberrantly growing cells of the CNS may be native to the CNS or derived from other tissues. Included among CNS disorders are cancer, infection, head trauma, spinal cord injury, multiple sclerosis, dementia with Lewy bodies, ALS, lysosomal storage disorders, psychiatric disorders, neurodegenerative disorders, stroke, epilepsy, and other acute and chronic disorders of the CNS.

Gliomas are the most common primary tumors of the central nervous system (CNS). Glioblastoma multiforme (GBM) is the most frequent and the most malignant type of glioma. There is a much higher incidence of GBM in adults than in children. According to the Central Brain Tumor Registry of the United States statistical report, GBM accounts for about 20% of all brain tumors in the USA (CBTRUS, 1998-2002). Other tumors of the CNS include, but are not limited to, other gliomas, including astrocytoma, including fibrillary (diffuse) astrocytoma, pilocytic astrocytoma, pleomorphic xanthoastrocytoma, and brain stem glioma, oligodendroglioma, and ependymoma and related paraventricular mass lesions, neuronal tumors, poorly differentiated neoplasms, including medulloblastoma, other parenchymal tumors, including primary brain lymphoma, germ cell tumors, and pineal parenchymal tumors, meningiomas, metastatic tumors, paraneoplastic syndromes, peripheral nerve sheath tumors, including schwannoma, neurofibroma, and malignant peripheral nerve sheath tumor (malignant schwannoma)

Epilepsy is the most common serious CNS disorder associated with the dysfunction of a particular neuronal population in the CNS (Shorvon, S., Epidemiology, classification, natural history, and genetics of epilepsy, Lancet 1990 Jul. 14; 336(8707):93-6; McNamara J., The neurobiological basis of epilepsy, Trends Neurosci 1992 October; 15(10):357-9). Severe, penetrating head trauma is associated with up to a 50% risk of leading to epilepsy. Other causes of epilepsy include stroke, infection and genetic susceptibility. A seizure is a neurological dysfunction which results from abnormal, excessive, hypersynchronous discharges from an aggregate of central nervous system neurons. A seizure can be manifested behaviorally (if motor systems are involved) or electrographically. Epilepsy describes a condition in which a person has recurrent seizures due to a chronic, underlying process. Although there are various epilepsy syndromes in which the clinical and pathologic characteristics differ the common underlying etiology is neuronal hyperexcitability. Thus, epilepsy encompasses disorders of central nervous system (CNS) hyperexcitability, characterized by chronic, recurrent, paroxysmal changes in neurological function that can be categorized according to electroencephalographic and clinical presentation (Dichter M., Basic mechanisms of epilepsy: targets for therapeutic intervention, Epilepsia 1997; 38 Suppl 9:S2-6).

Epileptic seizures are broadly categorized into two groups: focal (partial) and generalized seizures. Focal seizures arise from abnormal activity of a limited group of neurons in cortical or subcortical regions of the brain. The underlying structural abnormality or lesion can develop as a result of birth injury, head trauma, tumor, abscess, infarction, vascular malformation or genetic disease (Dichter 1997, lbid). The location of the focal activity can be identified by the clinical seizure presentation or may be cryptic. Equivalently, the active focus may not involve the lesion itself but may arise in adjacent or distant (but connected) neuronal populations, supporting the hypothesis of plastic synaptic reorganization underlying focal hyperexcitability. (See e.g. Prince D. A., Epileptogenic neurons and circuits. In: Jasper's Basic Mechanisms of the Epilepsies, Third Edition (1999), Delgado-Escueta A. V., et al., editors), Advances in Neurology 79: 665-684).

Focal seizures are termed "simple" if there is no apparent change in consciousness, otherwise they are termed "complex". Complex focal seizures involve the temporal lobe and limbic system, and are the most common manifestation of epilepsy in adults. Focal seizures that spread to become bilateral electrographically, with concomitant loss of consciousness and with or without motor manifestations, are said to be secondarily generalized. Primary generalized seizures initiate with bilateral electrographic activity, loss of consciousness, and with or without motor convulsions. Focal epilepsy can involve almost any part of the brain and usually results from a localized lesion of functional abnormality. Current therapy for focal epilepsy includes use of an EEG to localize abnormal spiking waves originating in areas of organic brain disease that predispose to focal epileptic attacks, followed by surgical excision of the focus to prevent future attacks.

Liposomal Formulations

Liposomal formulations described herein, e.g., pharmaceutical compositions comprising such formulations, may be formed in a variety of ways, including by active or passive loading methodologies. For example, one or more therapeutic drug(s) and/or diagnostic agent(s) may be encapsulated using a transmembrane pH gradient loading technique. General methods for loading liposomes with therapeutic drugs through the use of a transmembrane potential across the bilayers of the liposomes are well known to those in the art (e.g., U.S. Pat. Nos. 5,171,578; 5,077,056); and 5,192,549).

Briefly, for example, the lipids may be first dissolved in an organic solvent, such as ethanol, t-butanol, mixtures thereof, etc., and gently heated (e.g., 60° C.-70° C.). The lipid components used in forming the non-PEGylated liposomes may be selected from a variety of vesicle-forming lipids, typically including phospholipids and sterols (e.g., U.S. Pat. Nos. 5,059,421 and 5,100,662). For example, phospholipids derived from egg yolk, soybean or other vegetable or animal tissue, such as phosphatidylcholines, phosphatidylethanolamines, phosphatidic acid, phosphatidylserines, phosphatidylinositols, phosphatidylglycerols, sphingomyelins, etc.; mixtures thereof such as egg yolk phospholipid, soybean phospholipid, etc.; hydrogenation products thereof; and synthetic phospholipids such as dipalmitoylphosphatidlcholines, distearoylphosphatidylcholines, distearoylphosphatidylglycerols or the like may be used.

As described herein, the non-PEGylated anionic liposomes of the subject invention are a mixture of two or more non-PEGylated lipids, e.g., a neutral phospholipid and an anionic phospholipid. In one embodiment, the neutral phospholipid is chosen from the group composed of derivatives of phosphatidylcholine and their combinations, for example dipalmitoylphosphatidylcholine (DPPC), distearoylphosphatidylcholine (DSPC), dimyristoylphosphatidylcholine (DMPC) and their combinations. In one embodiment, the anionic phospholipid is selected from a group composed of derivatives of phosphatidylglycerol, dipalmitoyl phosphatidyl glycerol (DPPG), phosphatidylserine, phosphatidylinositol, phosphatidic acid and their combinations, for example, distearoyl phosphatidyl glycerol (DSPG) and a mixture of phosphatidylserine esters with different saturated fatty acids (PS). For stabilization of liposomes and other purposes, a sterol (e.g., cholesterol), α-tocopherol, dicetyl phosphate, stearylamine or the like may also be added.

To the dissolved lipids, a pre-heated aqueous solution may be added while vigorously mixing. For example, a solution containing 150-300 mM buffer may be added. Buffers that may be used include, but are not limited to, ammonium sulphate, citrate, maleate and glutamate. Following mixing, the resulting multilamellar vesicles ("MLVs") may be heated and extruded through an extrusion device to convert the MLVs to unilamellar liposome vesicles. The organic solvent used initially to dissolve the lipids may be removed from the liposome preparation by dialysis, diafiltration, etc.

One or more therapeutic drugs and/or diagnostic agents may be entrapped in the liposomes using transmembrane pH gradient loading. By raising the pH of the solution external to the liposomes, a pH differential will exist across the liposome bilayer. Thus, a transmembrane potential is created across the liposome bilayer and the one or more therapeutic drug and/or diagnostic agent is loaded into the liposomes by means of the transmembrane potential.

Generally, the therapeutic drug and/or diagnostic agent to lipid ratio is about 0.01 to about 0.5 (wt/wt). In one embodiment, therapeutic drug and/or diagnostic agent to lipid ratio is about 0.1. In another embodiment, the therapeutic drug and/or diagnostic agent to lipid ratio is about 0.3. In one embodiment, vesicles are prepared with a transmembrane ion gradient, and incubated with a therapeutic drug and/or diagnostic agent that is a weak acid or base under conditions that result in encapsulation of the therapeutic agent or diagnostic agent. In another embodiment vesicles are prepared in the presence of the therapeutic drug and/or diagnostic agent and the unencapsulated material removed by dialysis, ion exchange chromatography, gel filtration chromatography, or diafiltration.

A preferred embodiment for loading is based upon U.S. Pat. No. 5,192,549 and involves removing ammonium from the external media. The result creates a transmembrane ammonium concentration gradient that induces a pH gradient. The drug is added to the vesicles, and "remote" loaded following incubation at elevated temperatures.

In a preferred embodiment, with an agent that is essentially impermeable (e.g., a diagnostic agent such as gadodiamide), the agent is present in the buffer that is used to make the liposomes and becomes passively encapsulated at the time of vesicle formation. This preferred method also applies to other zwitterionic drugs such as methotrexate. In contrast, weak bases (and acids) can be remote loaded into liposomes.

The liposomal formulations described herein may be used for convection-enhanced delivery to central nervous system regions, and CED can achieve high tissue distribution volumes within the CNS. Accordingly, the liposomal formulations may be used for the treatment of CNS disorders. Such CNS disorders include, but are not limited to CNS tumors such as, e.g., glioblastoma, and disorders associated with dysfunction of neuronal cells such as, e.g., epilepsy.

Accordingly, a wide variety of therapeutic drugs used in the treatment of CNS disorders may be entrapped within the liposomal formulations described herein for use in methods described herein. Such therapeutic drugs include antitumor agents, toxins, biogenic agents (e.g., dopamine, serotonin), neurotrophic factors (e.g. GDNF, CDNF, MANF), etc.

In one embodiment, topoisomerase I inhibitors (including, but not limited to topoisomerase I/II inhibitors) are comprised within the liposomal formulations described herein. In one embodiment, the topoisomerase inhibitor is camptothecan or a derivative thereof. For example, in one embodiment, the therapeutic drug is a camptothecin derivative selected from the group consisting of 9-aminocamptothecin, 7-ethylcamptothecin, 10-hydroxycamptothecin, 9-nitrocamptothecin, 10,11-methlyenedioxycamptothecin, 9-amino-10,11-methylenedioxycamptothecin 9-chloro-10,11-methylenedioxycamptothecin, irinotecan, topotecan, 7-(4-methylpiperazinomethylene)-10,11-ethylenedioxy-20(S)-camptothecin, 7-(4-methylpiperazinomethylene)-10,11-methylenedioxy-20(S)-camptothecin and 7-(2-(N-isopropylamino)ethyl)-(20S)-camptothecin. In another embodiment, the camptothecin derivative is selected from the group consisting of irinotecan, topotecan, (7-(4-methylpiperazinomethylene)-10,11-ethylenedioxy-20(S)-camptothecin, 7-(4-methylpiperazinomethylene)-10,11-methylenedioxy-20(S)-camptothecin or 7-(2-(N-isopropylamino)ethyl)-(20S)-camptothecin. In another embodiment, the camptothecin is topotecan. It will be evident to those of ordinary skill in the art that, although certain agents are described as illustrative, numerous other agents are also suitable within the liposome compositions of the present invention.

Also contemplated for use herein are toxins, e.g., protein toxins, including μ-conotoxins (e.g., μ-conotoxin GIIIA, μ-conotoxin GIIIB, μ-conotoxin GIIIC, μ-conotoxin PIIIA, μ-conotoxin SmIIIA, μ-conotoxin KIIIA, etc.), ω-conotoxins (e.g., ω conotoxin GVIA (also referred to herein as "ω-conotoxin G" and "ω-CTX-G")), ω-conotoxin MVIIA (also referred to herein as "ω-conotoxin M" and "ω-CTX-M"), botulinum toxins (e.g., botulinum toxin A (also referred to herein as BTX-A), botulinum toxin B (also referred to herein as "BTX-B", botulinum toxin C1, botulinum toxin D, botulinum toxin E, botulinum toxin F, etc.), conantokin peptides (e.g., conantokin G, conantokin T, conantokin L, conantokin S1, conantokin Oc, conantokin Gm, conantokin Ca2, conantokin Ca1, and conantokin Qu), derivatives thereof, and pharmaceutically acceptable salts thereof.

In one embodiment, conotoxins derived from the venom of Conus snails can be delivered using the subject formulations. The active components of the venom are small peptide toxins, usually 10 to 30 amino acid residues in length and typically highly constrained due to their high density of disulphide bonds. The venom components act on voltage-gated ion channels, ligand-gated ion channels, and G protein-coupled receptors. The pharmaceutical selectivity of conotoxins is at least in part determined by specific disulfide bond frameworks combined with hypervariable amino acids within disulfide loops. Due to the high potency and exquisite selectivity of the conotoxin peptides, several have been evaluated for the treatment of human disorders and one of these ω-conotoxin MVIIA (ziconotide), an N-type calcium channel blocker, is currently used to treat pain in human patients by means of an implantable, programmable pump with a catheter threaded into the intrathecal space.

In certain embodiments of the present invention, the antiepileptic drug formulation comprises ω-conotoxins such as ω conotoxin GVIA, ω-conotoxin MVIIA and ω-conotoxin CVID. See, e.g., Gasior et al. J. Pharmacol. Exp. Ther. 323: 458-68 (2007). In alternative embodiments, the antiepileptic drug formulation comprises μ-conotoxins such as μ-conotoxin GIIIA, μ-conotoxin GIIIB, μ-conotoxin GIIIC, μ-conotoxin PIIIA, μ-conotoxin SmIIIA, μ-conotoxin KIIIA. See, e.g., Zhang et al., J. Biol. Chem. 282:30699-30706 (2007). Other embodiments utilize derivatives or pharmaceutically acceptable salts of the conotoxins, as described herein.

Also contemplated for use herein are botulinum toxins derived from *Clostridium botulinum*. Seven immunologically distinct botulinum neurotoxins have been characterized, these being respectively botulinum neurotoxin serotypes A, B, C1, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Accordingly, non-type A botulinum toxin serotypes may have a lower potency and/or a shorter duration of activity as compared to botulinum toxin type A.

Although all the botulinum toxins serotypes apparently inhibit release of the neurotransmitter at the neuromuscular junction, they do so by affecting different neurosecretory proteins and/or cleaving these proteins at different sites. For example, botulinum types A and E both cleave the 25 kilo-Dalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes.

In vitro studies have indicated that botulinum toxin inhibits potassium induced release of various neurotransmitters from primary cell cultures and brain synaptosome preparations. Glutamate is the neurotransmitter responsible for the bulk of synaptic excitation in the brain, and it is believed to be integral to the generation and spread of seizure discharges. It has been reported that botulinum toxin inhibits the evoked release of glutamate in primary cultures of spinal cord neurons and that in brain synaptosome preparations botulinum toxin inhibits the release of glutamate and other neurotransmitters.

In some embodiments of the present invention, the antiepileptic drug is botulinum toxin A or botulinum toxin B. In other embodiments, the toxin is a fragment or an analog of botulinum toxin A or botulinum toxin B that possesses biological activity of the parent toxins. In other embodiments, the toxins are modified to bind specifically to appropriate targets on brain neurons. In some embodiments, recombinant techniques are used to produce the clostridial neurotoxins or their fragments or analogs.

Also contemplated for use in the present invention are conantokins, including those described in U.S. Pat. Nos. 6,172,041 and 6,399,574, the disclosures of which are expressly incorporated by reference herein.

Diagnostic agents may also be entrapped within liposomes as described herein. Suitable agents include a paramagnetic ion for use with MRI, referred to herein as "MRI magnets.". Suitable metal ions include those having atomic numbers of 22-29 (inclusive), 42, 44 and 58-70 (inclusive) and have oxidation states of +2 or +3. Examples of such metal ions are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III).

In embodiments wherein X-ray imaging (such as CT) is used to monitor CED, the diagnostic agent may comprise a radiopaque material. Suitable radiopaque materials are well known and include iodine compounds, barium compounds, gallium compounds, thallium compounds, and the like. Specific examples of radiopaque materials include barium, diatrizoate, ethiodized oil, gallium citrate, iocarmic acid, iocetamic acid, iodamide, iodipamide, iodoxamic acid, iogulamide, iohexyl, iopamidol, iopanoic acid, iprocemic acid, iosefamic acid, ioseric acid, iosulamide meglumine, iosumetic acid, iotasul, iotetric acid, iothalamic acid, iotroxic acid, ioxaglic acid, ioxotriroic acid, ipodate, meglumine, metrizamide, metrizoate, propyliodone, and thallous chloride.

As described herein, the liposomal formulations are suitable for convection-enhanced delivery.

Convection-Enhanced Delivery

Convection-enhanced delivery (CED) is a direct intracranial drug delivery technique that utilizes a bulk-flow mechanism to deliver and distribute macromolecules to clinically significant volumes of solid tissues. CED offers a greater volume of distribution than simple diffusion and is designed to direct a therapeutic drug to a specific target site. See, e.g., U.S. Pat. No. 5,720,720, the disclosure of which is expressly incorporated by reference herein. Briefly, convection-enhanced delivery (CED) is a method that circumvents the blood-brain barrier and allows large molecular weight substances, such as drug-loaded liposomes, to be administered uniformly and in a controlled fashion within a defined region of brain. (See for example, U.S. Ser. No. 11/740,548, incorporated herein in its entirety by reference). CED may be used to administer a fluid pharmacological agent (e.g., a liposomal formulation) to a solid tissue (e.g., a brain tumor) through direct convective interstitial infusion and over a predetermined time by inserting a catheter directly into the tissue; and administering the agent under pressure through the catheter into the interstitial space at a predetermined flow rate, e.g., from about 0.1 µL/min to about 12 µL/min.

As detailed herein, Applicants have discovered that CED may be effectively used for the delivery of therapeutic drugs and also optionally diagnostic agents encapsulated in non-PEGylated liposome formulations, where the formulations comprise or consist essentially of a mixture of at least one neutral saturated phospholipid and at least one anionic saturated lipid. As described in the Examples section, CED of a composition comprising at least one therapeutic drug (e.g., topotecan) and/or diagnostic agent encapsulated in a non-PEGylated liposome formulation as described herein increases the volume of distribution and dramatically improves the serum half-life of the therapeutic drug.

A suitable apparatus that may be used for administration of a liposomal formulation (e.g., as pharmaceutical compositions) may comprise a pump device that contains a reservoir filled with the liposomal formulation. The pump may be external to the body or implanted within the body. The pump may be connected to a catheter, which may be implanted into discrete tissue(s) within the CNS. The pump may be activated to release the liposomal formulation at a pressure and flow rate that causes the solute to convect within the specific tissue.

The duration and other parameters of the infusion may be adjusted to distribute the liposomal formulation throughout the discrete tissue(s) to areas adjacent to the discrete tissue(s), e.g., not into the cerebrospinal fluid. Depending upon the size and shape of the discrete tissue(s), it may be necessary to use multiple implanted infusion catheters or to use an infusion catheter with multiple solution exit ports.

Using CED, a liposomal formulation may be distributed by slow infusion into the interstitial space under positive pressure through a fine cannula. Bulk flow driven by hydrostatic pressure derived from a pump may be used to distribute the liposomal formulation within the extracellular spaces of the CNS. Because the use of CED permits distribution of liposomal formulations directly within nervous tissues via the tip of a cannula, the blood-brain barrier is bypassed and discrete tissues in the central nervous system may be targeted, including discrete tissue defined, e.g., as cancerous or identified as for resection by a conventional presurgical evaluation, and in different foci if more than one focus are in need of treatment. Based on the properties of bulk flow, CED may be used to distribute liposomal formulations reliably, safely, and homogeneously over a range of volumes. See for example U.S. Ser. No. 11/740,508. Further, CED does not cause structural or functional damage to the infused tissue and provides greater control over the distribution of the liposomal formulation. Additionally, liposomal formulations may be distributed homogeneously throughout a distribution volume that is proportional to the infusion volume regardless of the molecular weight of the liposomes comprised in the liposomal formulations.

In one embodiment, an ultrafine delivery catheter (constructed of polyurethane and fused silica in a novel "step" design) may be permanently implanted with a transcutaneous port. The novel catheter design may be rapidly biointegrated and may be internally sealed and filtered to prevent bacterial ingress and capped for further safety. A liposomal formulation may be infused as needed through the port of this catheter system.

In one embodiment described herein, CED may be applied with a small diameter catheter permanently implanted in the brain region using an infusion pump. Liposomal formulations to be administered may be prepared as an aqueous isotonic solution, or other appropriate formulation. During the administration (e.g., infusion), the liposomal solution may flow within the extracellular space and cause minimal to no damage to the brain tissue.

In one embodiment, an ultrafine (0.2 mm OD at tip), minimally traumatic catheter system specially designed for transcutaneous CED delivery may be used. The catheter system has a step design, which may eliminate solution reflux along the sides of the catheter. Such solution leakage is a major problem with straight-sided catheters. The catheter system may be constructed of polyurethane and fused silica or Peek Optima so that it is highly biocompatible and does not interfere with MRI signals. Treatment of CNS disorders may require readministration of a liposomal formulation at varying intervals, e.g., weekly intervals, monthly intervals, etc. For example, see U.S. Ser. No. 11/740,124, the disclosure of which is expressly incorporated by reference herein The transcutaneous port may remain capped during the interval period. Multiple catheter designs are feasible so that it may be possible to perfuse a larger area of discrete tissue(s) than is feasible with a single catheter. It has been found that the volume of distribution of liposomes after CED infusion is linearly related to the solution volume infused.

An especially preferred cannula is disclosed in Krauze et al., J Neurosurg. November 2005; 103(5):923-9, incorporated herein by reference in its entirety, as well as in U.S. Patent Application Publication No. US 2007/0088295 A1, incorporated herein by reference in its entirety, and United States Patent Application Publication No. US 2006/0135945 A1, incorporated herein by reference in its entirety.

In one embodiment, CED comprises an infusion rate of between about 0.1 µL/min and about 10 µL/min. In another embodiment, CED comprises an infusion rate of greater than about 0.1 µL/min to about 0.3 µL/min, e.g., about 0.2 µL/min, more preferably greater than about 0.7 µL/min, more preferably greater than about 1 µL/min, more preferably greater than about 1.2 µL/min, more preferably greater than about 1.5 µL/min, more preferably greater than about 1.7 µL/min, more preferably greater than about 2 µL/min, more preferably greater than about 2.2 µL/min, more preferably greater than about 2.5 µL/min, more preferably greater than about 2.7 µL/min, more preferably greater than about 3 µL/min, and preferably less than about 12 µL/min, more preferably less than about 10 µL/min.

In a preferred embodiment, CED comprises incremental increases in flow rate, referred to as "stepping" or up-titration, during delivery. Preferably, stepping comprises infusion rates of between about 0.1 µL/min and about 10 µL/min.

In a preferred embodiment, stepping comprises infusion rates of greater than about 0.5 µL/min, more preferably greater than about 0.7 µL/min, more preferably greater than about 1 mL/min, more preferably greater than about 1.2 µL/min, more preferably greater than about 1.5 µL/min, more preferably greater than about 1.7 µL/min, more preferably greater than about 2 µL/min, more preferably greater than about 2.2 µL/min, more preferably greater than about 2.5 µL/min, more preferably greater than about 2.7 µL/min, more preferably greater than about 3 µL/min, and preferably less than about 12 µL/min, more preferably less than about 10 µL/min.

Treatment methods herein also preferably comprise neuroimaging via a diagnostic agent, preferably MRI, for target localization and guided cannula placement. Preferably a stereotactic holder is used in conjunction with neuroimaging of a diagnostic agent to provide for guided cannula placement at or proximal to a target neuronal population. A tracing agent is preferably detectable by magnetic resonance imaging (MRI) or X-ray computed tomography. The distribution of tracing agent is monitored and used as an indirect measure of the distribution of high molecular weight neurotherapeutic. This monitoring is done to detect unwanted delivery of infusate to non-target tissue and to verify that the high molecular weight neurotherapeutic is reaching target tissue and achieving an effective concentration therein.

In one embodiment, the diagnostic agent is separate from the therapeutic agent. The diagnostic agent is distributed at a rate that correlates with that of the therapeutic agent and thus is an indirect indicator of therapeutic distribution. In a preferred embodiment, the diagnostic agent and the therapeutic agent are separately administered but encapsulated by the same non-PEGylated anionic liposomal formulation, which confers highly similar distribution characteristics. In another embodiment, the diagnositic agent and the therapeutic agent are co-administered.

Treatment methods herein also preferably comprise neuroimaging for monitoring infusate distribution. In a preferred embodiment, a treatment method comprises the use of MRI for monitoring distribution of an infused pharmaceutical composition of the invention, wherein the pharmaceutical composition comprises an MRI magnet.

EXAMPLES

Example 1

Comparison of PEGylated and Non-PEGylated Liposome Formulations for CED

Example 1.1

Materials and Methods

Example 1.1.1

DSPC/CHOL (60/40 Mole Ratio)

Weigh 26.1 mg DSPC (MW 790; lot # C3L006; actual wt. 26.2 mg)+8.5 mg cholesterol (MW 387; lot # CH1S003; actual wt. 8.8 mg).

Dissolve in 0.5 ml chloroform; add 75 µl 5 mg/ml RhPE in EtOH (0.2 mole % of phospholipid).

Dry down the sample under nitrogen while vortexing to form a thin film. Finish drying under vacuum for 1 hour.

Rehydrate the lipids at 60° C. in 1.5 ml HBS (5 mM HEPES-145 mM NaCl pH 7.0; 0.1192 g HEPES [MW 238.3]+0.8475 g NaCl [MW 58.45], pH adjusted with NaOH, volume made up to 100 ml) to form MLVs.

Extrude at 60° C. through 2×100 nm filters to obtain LUVs (target size 100-120 nm).

Assay for phosphate—dilute to 20 mM phospholipids.

Vial in 2.0 ml serum vials (previously depyrogenated).

Example 1.1.2

DSPC/CHOL/PEG$_{2000}$DSPE (59.5/40/0.5 Mole Ratio)

Weigh 25.8 mg DSPC (MW 790; lot # C3L006; actual wt. 25.6 mg)+8.5 mg cholesterol (MW 387; lot # CH1S003; actual wt. 8.7 mg)+0.75 mg PEG$_{2000}$DSPE (MW 2774; lot # PPE2011809; actual wt. 50 µl of 15 mg/ml solution in CHCl$_3$; prepare 18 mg [actual 17.9 mg] in 1.2 ml CHCl$_3$).

Dissolve in 0.5 ml chloroform; add 75 µl RhPE (0.2 mole % of phospholipid).

Dry down the sample under nitrogen while vortexing to form a thin film. Finish drying under vacuum for 1 hour.

Rehydrate the lipids at 60° C. in 1.5 ml HBS (5 mM HEPES-145 mM NaCl pH 7.0) to form MLVs.

Extrude at 60° C. through 2×100 nm filters to obtain LUVs (target size 100-120 nm).

Assay for phosphate—dilute to 20 mM phospholipids. Vial in 2.0 ml serum vials (previously depyrogenated).

Example 1.1.3

DSPC/CHOL/PEG$_{2000}$DSPE (55/40/5 Mole Ratio)

Weigh 23.9 mg DSPC (MW 790; lot # C3L006; actual wt. 23.8 mg)+8.5 mg cholesterol (MW 387; lot # CH1S003; actual wt. 8.6 mg)+7.5 mg PEG$_{2000}$DSPE (MW 2774; lot # PPE2011809; actual wt. 5000 of 15 mg/ml solution in CHCl$_3$).

Dissolve in 0.5 ml chloroform; add 75 µl RhPE (0.2 mole % of phospholipid).

Dry down the sample under nitrogen while vortexing to form a thin film. Finish drying under vacuum for 1 hour.

Rehydrate the lipids at 60° C. in 2.0 ml HBS (5 mM HEPES-145 mM NaCl pH 7.0) to form MLVs.

Extrude at 60° C. through 2×100 nm filters to obtain LUVs (target size 100-120 nm).

Assay for phosphate—dilute to 20 mM phospholipids.

Vial in 2.0 ml serum vials (previously depyrogenated).

Example 1.1.4

DSPC/CHOL/NG-DOPE (55/40/5 Mole Ratio)

Weigh 23.9 mg DSPC (MW 790; lot # C3L006; actual wt. 24.2 mg)+8.5 mg cholesterol (MW 387; lot #CH1S003; actual wt. 8.9 mg)+2.4 mg NG-DOPE (MW 880.13; lot #050328L; actual wt. 2.4 mg).

Dissolve in 0.5 ml chloroform; add 75 µl RhPE (0.2 mole % of phospholipid).

Dry down the sample under nitrogen while vortexing to form a thin film. Finish drying under vacuum for 1 hour.

Rehydrate the lipids at 60° C. in 2.0 ml HBS (5 mM HEPES-145 mM NaCl pH 7.0) to form MLVs.

Extrude at 60° C. through 2×100 nm filters to obtain LUVs (target size 100-120 nm).

Assay for phosphate—dilute to 20 mM phospholipids.

Vial in 2.0 ml serum vials (previously depyrogenated).

Example 1.1.5

DSPC/PEG$_{2000}$DSPE (99/1 Mole Ratio)

Weigh 25.8 mg DSPC (MW 790; lot #C3L006; actual wt. 26.1 mg)+0.9 mg PEG$_{2000}$DSPE (MW 2774; lot # PPE2011809; actual wt. 60 µl of 15 mg/ml solution in CHCl$_3$).

Dissolve in 0.5 ml chloroform; add 75 µl RhPE (0.2 mole % of phospholipid).

Dry down the sample under nitrogen while vortexing to form a thin film. Finish drying under vacuum for 1 hour.

Rehydrate the lipids at 60° C. in 1.5 ml HBS (5 mM HEPES-145 mM NaCl pH 7.0) to form MLVs.

Extrude at 60° C. through 2×100 nm filters to obtain LUVs (target size 100-120 nm).

Assay for phosphate—dilute to 20 mM phospholipids.

Vial in 2.0 ml serum vials (previously depyrogenated).

Example 1.1.6

DSPC/PEG$_{2000}$DSPE (95/5 Mole Ratio)

Weigh 24.8 mg DSPC (MW 790; lot #C3L006; actual wt. 24.6 mg)+4.6 mg PEG$_{2000}$DSPE (MW 2774; lot #PPE2011809; actual wt. 307 µl of 15 mg/ml solution in CHCl$_3$).

Dissolve in 0.5 ml chloroform; add 75 µl RhPE (0.2 mole % of phospholipid).

Dry down the sample under nitrogen while vortexing to form a thin film. Finish drying under vacuum for 1 hour.

Rehydrate the lipids at 60° C. in 1.5 ml HBS (5 mM HEPES-145 mM NaCl pH 7.0) to form MLVs.

Extrude at 60° C. through 2×100 nm filters to obtain LUVs (target size 100-120 nm).

Assay for phosphate—dilute to 20 mM phospholipids.

Vial in 2.0 ml serum vials (previously depyrogenated).

Example 1.1.7

DSPC/DSPG (70/30 Mole Ratio)

Weigh 18.2 mg DSPC (MW 790; lot #C3L006; actual wt. 18.1 mg)+7.4 mg DSPG (MW 745; lot #G3L006; actual wt. 7.6 mg)

Dissolve in 0.5 ml chloroform/MeOH (9/1, v/v); add 75 μl RhPE (0.2 mole % of phospholipid).

Dry down the sample under nitrogen while vortexing to form a thin film. Finish drying under vacuum for 1 hour.

Rehydrate the lipids at 60° C. in 2.0 ml HBS (5 mM HEPES-145 mM NaCl pH 6.5) to form MLVs.

Extrude at 60° C. through 2×100 nm filters to obtain LUVs (target size 100-120 nm).

Assay for phosphate—dilute to 20 mM phospholipids.

Vial in 2.0 ml serum vials (previously depyrogenated).

Example 1.1.8

Phosphate Assay

Dilute samples 1/50 (20 μl to 1.0 ml) with water to make concentration ~0.4 mM.

Aliquot 3×200 μl of each diluted sample.

Assay for phosphate as per ACM-010.

Examples 1.2

Results

See FIGS. 1A-1F.

Example 2

Pharmacology Assessment of Nanoliposomal Compounds Delivered Intracerebrally to the Rodent Brain Example 2.1

Materials and Methods

Example 2.1.1

Test Articles

The experiments in this example were performed with research grade material of both liposomal-topotecan (Ls-TPT) and liposomal gadodiamide (Ls-GD). Topotecan (TPT) for free topotecan formulation and for Ls-TPT preparation was obtained from Hisun Pharmaceuticals (Taizhou City, Zhejiang, China). Ls-TPT was provided by Northern Lipids Inc (Burnaby, BC, Canada). In brief, liposomes were composed of distearoylphosphatidylcholine (DSPC), distearoylphosphatidylglycerol (DSPG), and cholesterol at a 7:2:1 molar ratio with 75 to 90 nm target size. Topotecan was remotely loaded (actively encapsulated) into liposomes in response to a transmembrane pH gradient using internal and external buffers consisting of ammonium sulfate 250 mM pH 5.5 and histidine 5 mM/NaCl 145 mM pH 6.0 respectively. Topotecan concentrations of 0.67 and 2.0 mg/mL with a 0.1 and 0.3 (w/w) drug:lipid ratio were respectively targeted assuming a 90-95% drug encapsulation efficiency. A constant total lipid concentration target of 6.7 mg/mL was maintained in both formulations. The manufacturing process is described in details in Example 2.1.2.

Gadodiamide (GD) for Ls-GD preparation was obtained from Beijing SHLHT Science & Trade (Beijing, China). Ls-GD was prepared similarly to Ls-TPT, except that the gadodiamide was passively encapsulated in the liposomes. The internal buffer solution consisted of 520 mM gadodiamide, pH 3.5 instead of 250 mM ammonium sulfate, pH 5.5. Assuming an encapsulation efficiency of 4-6%, a gadodiamide to lipid ratio of 0.3 (w/w) and a particle size of 75 to 120 nm were targeted. The final formulation lipid and gadodiamide concentrations were 51.1 mg/mL and 17.0 mg/mL, respectively.

Unless otherwise stated, Ls-TPT test articles were stored frozen (−20 to −30° C.). Dosing solutions were prepared fresh on the day of dosing and kept at room temperature. Appropriate dilutions with 5 mM histidine, 145 mM NaCl pH 6.0, 300 mM sucrose of stock solution (Ls-TPT and free topotecan) were performed to yield the desired concentrations. Fresh vials of the stock test article solution were used on each dosing day.

Example 2.1.2

Liposome Manufacturing Process

The amount of lipid required for the batch was calculated and the lipid powders were weighed into weighing boats. A solvent solution consisting of t-butanol, ethanol and water (45:45:10 vol/vol) was prepared and heated to 70° C. While stirring, the lipid powders were added to the solvent solution. The solvent was maintained at 70° C. and stirred until all the lipids were dissolved (~1 hour). The concentration of lipids in solution at that point was 320 mg/mL. A 250 mM solution of ammonium sulphate was prepared (volume was nine times that of the lipid solvent solution) and heated to 70° C. After the ammonium sulphate had reached temperature, the lipid solution was poured into the ammonium sulphate solution while stirring to generate multilamellar vesicles (MLVs). The MLVs were maintained at 70° C. and extruded through 4-stacked polycarbonate filters with 80 nm pores. Two passes were required to generate large unilamellar vesicles (LUVs) of the desired size (75-90 nm mean diameter). The size of the liposomes was measured by QELS following each pass through the extruder. The LUVs were maintained at 70° C. until they had been reduced to the desired size and were then diluted with histidine saline pH 6.0 buffer to a concentration of 5% solvent as the LUVs were unstable below their phase transition temperature of ~55° C. in 10% solvent. The LUVs were then re-concentrated to ~50 mg/mL total lipid by ultrafiltration and subsequently diafiltered against 10 wash volumes of 10 mM histidine, 145 mM NaCl buffer to remove the solvent and exchange the external buffer from ammonium sulphate to pH 6.0 histidine buffer. This buffer exchange resulted in the generation of a transmembrane pH gradient that was used to load topotecan into the preformed liposomes. The total lipid concentration was then determined by phosphate assay. After determining the total amount of lipid, the amount of topotecan required to achieve a 0.1:1 or 0.3:1 (w/w) drug:lipid ratio is calculated by multiplying the total mass of lipid by 0.1 and 0.3 respectively. To achieve a final drug:lipid ratio of 0.1:1 or 0.3:1 (w/w) a loading efficiency of 90% was assumed. After calculating the total amount of topotecan required, the powder was weighed into a clean bottle. The LUV suspension was heated to 60° C. and the topotecan powder added. The topotecan was allowed to load for 60 minutes following drug addition to ensure optimal loading into the liposomes. Following drug loading, the un-encapsulated topotecan was removed by diafiltration employing 5-wash volumes of a 5 mM histidine, 300 mM sucrose pH 6.0 buffer. This step also served to exchange the external buffer from sodium chloride solution to sucrose which acted as a cryo-protectant and allowed the formulation to be frozen without changing its physical characteristics. The estimated lipid content at this stage was 8.3 mg/mL (for the 0.3:1 drug:lipid ratio). The formulation was heated to 50° C. and passed through a 0.2 µm syringe filter. The product was then vialed. The product was finally frozen, completing the manufacturing process.

Example 2.1.3

Animals and Grouping

Adult male Sprague-Dawley rats (Harlan, Indianapolis, Ind.) (batches 120806 and 010507) weighing 250-350 g were used.

For the formulation screening component of this example, the animals were divided in 4 groups based on Ls-TPT formulations or free topotecan as outlined in Table 1.

TABLE 1

Group Assignments and Dosing for Formulation Screening

| Group | TPT concentration (µg/µL) | GD concentration (µg/µL) | Injection volume per rat (µL) | Sacrifice time points (hours, days) | Number of time points | Planned number to be euthanized at each time point | Total number of animals to be used |
|---|---|---|---|---|---|---|---|
| F1 | 0.5 | 1.15 | 40 | 1 h, 6 h, 2 d, 4 d, 7 d | 5 | 3 | 15 |
| F2 | 0.5 | 1.15 | 40 | 1 h, 6 h, 2 d, 4 d, 7 d | 5 | 3 | 15 |
| F3 | 0.5 | 1.15 | 40 | 1 h, 6 h, 2 d, 4 d, 7 d | 5 | 3 | 15 |
| F4 | 0.5 | 0 | 40 | 1 h, 6 h, 2 d, 4 d, 7 d | 5 | 3 | 15 |
| | | | | Total rats | | | 60 |

F1: DSPC/Chol 0.1 D:L ratio Ls-TPT at 0.5 mg/mL + Ls-GD at 1.15 mg/mL
F2: DSPC/DSPG/Chol 0.3 D:L ratio Ls-TPT at 0.5 mg/mL + Ls-GD at 1.15 mg/mL
F3: DSPC/DSPG/Chol 0.1 D:L ratio Ls-TPT at 0.5 mg/mL + Ls-GD at 1.15 mg/mL
F4: Free topotecan at 0.5 mg/mL
DSPC/DSPG = distearoylphosphatidylcholine/distearoylphosphatidylglycerol
Chol = cholesterol
D:L ratio = drug:lipid ratio (w/w)
Ls-TPT = liposomal topotecan
Ls-GD = liposomal gadodiamide Rats were assigned to groups based on body weight in a manner to achieve comparable group mean body weights and standard deviations. The groups were then to be randomly assigned to treatment and time point.

Example 2.1.4

Surgical Procedures

Rats were anesthetized with either isoflurane (5% for induction; 2.5 to 3.0% for maintenance during surgery) inhalation or a combination of ketamine (60 mg/kg) and xylazine (8 mg/kg) via an intraperitoneal injection. The skin over the cranium was shaved and the animal mounted in a stereotaxic frame with the head positioned by the use of ear bars and the incisor bar. Aseptic techniques were used for all surgical procedures. The skin was disinfected with 70% alcohol followed by betadine solution. A longitudinal incision was made in the skin on top of the skull and blunt dissection was made to remove connective tissue overlying the skull. Craniectomy was performed using a small electric dental drill with 1-mm diameter burr holes, 0.5 mm anterior and 3 mm left and right from the bregma. A fused silica cannula (OD 168 µm, ID 102 µm) (PolyMicro Technologies, Phoenix, Ariz.) connected to an automated pump (BASi, Inc., West Lafayette, Ind.) was used for CED and was lowered to the dorso-ventral appropriate coordinates (−4.5 to −5 mm with the tooth bar at −3.3 mm). Dorso-ventral coordinates were calculated from the pial surface. The cannula was inserted into a 27-gauge needle connected with a 10-µL Hamilton syringe and secured with superglue on the tubing. The test article was injected bilaterally at one site into each striatum. A progressive infusion rate increment was used in this study to achieve a 20 µL dose per hemisphere with 0.2 µL/min (15 min) followed by 0.5 µL/min (10 min) and 0.8 µL/min (15 min). Following infusion completion, the cannula was left in place for 5 minutes to minimize outflow of infusate, and then slowly withdrawn.

Following completion of the procedure, the rats were maintained in a draft free environment, and kept warm via heating lamp or water bottle or other appropriate warming methods and monitored during anesthesia recovery. Buprenorphine was administered subcutaneously on an as needed basis. Rats were allowed to recover in the procedure room prior to return to their home cages.

Example 2.1.5

Tissue Collection and Processing

At designated time points animals were anesthetized with isoflurane (2.5%), followed by intracardiac perfusion with 0.9% saline.

A complete gross necropsy of all animals found dead or sacrificed (scheduled and unscheduled) during the study was performed on the carcass and muscular/skeletal system, all external surfaces and orifices, cranial cavity and external surface of the brain, neck with associated organs and tissues, thoracic, abdominal and pelvic cavities with their associated organs and tissues.

The brains were removed, placed on ice and the striata dissected using a dorsal approach and the tissue frozen in liquid nitrogen. The tissue was subsequently homogenized with an equal volume of water (1:1 v/v) and then extracted with methanol and stored at −70° C. until shipment to the Sponsor. Tail vein blood was collected (1.0 mL) for the formulation tissue and plasma pharmacokinetics component of this Example.

Example 2.1.6

HPLC

High performance liquid chromatography (HPLC) of total topotecan (free and liposome-encapsulated) in brain tissue and in plasma was performed by Northern Lipids Inc. (Burnaby, BC, Canada) using an isocratic reversed phase HPLC/UV method. Method details were as follows. Briefly, the animals (n=3) were sacrificed at 1 and 6 hours, 2, 4 and 7 days. The brains were removed, placed on ice, the striata dissected using a dorsal approach and the tissue frozen in liquid nitrogen. Equal volume of ice cold water (1:1 w/w) was added and the thawed tissue was homogenized (Biospec) mechanically for 2 minutes and frozen. The frozen homogenate was shipped to NLI for analysis. Two hundred µL of the thawed homogenate samples were transferred to an Eppendorf tube containing 800 µL of cold methanol (1:4) and centrifuged at 12,000 rpm for 2-5 minutes. The supernatant solution, 200 µL, was placed in an autosampler vial for immediate analysis (or stored at −70° C. until analysis up to 3 months) for analysis by high-performance liquid chromatography (HPLC) using a validated reversed phase HPLC methods by Northern Lipids Inc, Burnaby, BC, Canada. For TPT, standards were freshly prepared for the lactone form utilizing methanol:water:trifluoroacetic acid (40:60:0.02) and for the carboxylate form, 20 mM borate buffer: Methanol (60:40). Analysis was conducted on a Waters 2690/5 Separation Module and Empower software HPLC system with a C18 reverse-phase silica column [Phenomenex Inc. Luna C-18(2) column, 250 mm×4.6 mm inner diameter, 5 µm particle size, ambient temperature] preceded by a C18 security guard cartridge (Phenomenex Inc., 4×3.0 mm). Samples were placed in an autosampler tray at 5±3° C., a sample injection volume of 30 to 50 µL was used, and the column was eluted at a flow rate of 1.0 mL/min with a mobile phase consisting of mobile phase A: 3% triethylamine acetic acid buffer, pH 5.5, (TEAA) and mobile phase B: acetonitrile:3% TEAA (50:50). Gradient elution initial 78:22 A:B to 50:50 A:B in 5 min, held 3 min, back to initial in 0.5 min, total run time 15 min. Topotecan detected by a Waters 2475 Multi λ fluorescence detector (excitation 380 nm, emission 520 nm). Typical retention time for topotecan carboxylate and lactone forms was 5.5 and 7.5 min, respectively. The method has good sensitivity and linearity over the range of 0.8 ng/mL to 240 ng/mL. The extraction method recovery factor for TPT was 0.9.

Example 2.1.7

Early Death/Unscheduled Sacrifice

If an animal died on study, the time of death was estimated as closely as possible and recorded, and necropsy was performed as soon as possible. If the necropsy could not be performed immediately, the animal was refrigerated (not frozen) to minimize tissue autolysis. The necropsy was performed no later than 12 hours after death.

If an animal appeared in poor condition or in extremis, it could be euthanized. If possible, blood or other specimens were collected and analyzed as appropriate (e.g., for clinical pathology parameters) to help reveal the cause of malaise/morbidity.

Example 2.1.8

Statistical Methods

Descriptive statistics for continuous (N, mean and standard deviation) and categorical (N, %) data are presented both in tabular form and graphically, where appropriate. Pharmacokinetic (PK) parameters that included tissue half-life of the drug (t1/2), clearance (CL), mean residence time (MRT) in the brain, and area under the concentration versus time curve (AUC) were all determined by non-compartmental pharmacokinetics data analysis utilizing WinNonlin 5.0 (Pharsight Corporation, Mountain View, Calif., USA).

Example 2.1.9

Animal Care

Each animal was identified by a numbered ear tag and by cage cards. Upon arrival to the test facility, study animals were allowed to acclimatize to their housing room for a minimum of 3 days prior to study procedures. Animals were observed during the routine husbandry by the husbandry staff within their cages at least once daily throughout the study. Each animal was observed for changes in general appearance of health. Any signs of illness were promptly reported to the responsible veterinarian and study director.

Body weights were measured prior to drug infusion and planned sacrifice at 2, 4, 7, and 10 days.

Food consumption was assessed daily for each animal by the husbandry staff, beginning on the day prior to the surgery date until sacrifice. Food consumption was assessed by visual observation of the daily food left over. Evidence of fasting or dehydration was reported to the attending veterinarian and to a study personnel and the appropriate action was taken.

Example 2.2

Results

Example 2.2.1

Deviations

Two animal batches (batches 120806 and 010507) were used for the study. After the 6 hour, 2 day, 4 day and 7 day time points were performed and animals sacrificed, cardiomegaly was observed on gross necropsy at the time of transcardiac perfusion in a few animals sacrificed at different time points. In order to determine whether the cardiomegaly observed was related to the test article or the animal batch/strain, a different animal batch (batch 010507) was used the for 1 hour time point and 15 animals from the initial batch (batch 120806) were used as control. The control group did not have any surgical procedures or receive any test article.

Example 2.2.2

Formulation Screening Pharmacokinetics

The planned number of animals (60) for this study component was tested. No significant weight loss (≥10%) was observed between baseline and sacrifice for the time points where weight was assessed prior to sacrifice (2 d, 4 d, 7 d). Four animals at the 1 hour time point had to be replaced; two died from anesthesia, one woke up during test article infusion (formulation 3) and had to be euthanized, and one animal stopped breathing during burr hole drilling. None of the animals showed findings at gross necropsy. No animals at the 6 hour time point had to be replaced. One animal at the 2 day time point died from anesthesia and had to be replaced. One animal at the 4 day time point had to be replaced as it was mistakenly sacrificed as a control animal (3 days after infusion of formulation 3). Three animals at the 7 day time point had to be replaced as they were dosed with an incorrect preparation of formulation 1 and could not therefore be included in the analyses. Infusions were uneventful except for one animal assigned to formulation 4 and 1 hour time point in which leakage of the infusion system was observed 27 minutes into the 40 minute infusion. As described in Example 2.2.1, a total of 15 animals were used as control and did not undergo any intervention. A summary of animal disposition can be found in Table 3.

TABLE 3

Animal Disposition Summary

| Group | Control | Time point | | | | | Total number of animals |
|---|---|---|---|---|---|---|---|
| | | 1 hour | 6 hour | 2 day | 4 day | 7 day | |
| F1 | 0 | 3 | 3 | 3 | 3 | 6 (3) | 18 (3) |
| F2 | 0 | 3 | 3 | 3 | 3 | 3 | 15 |
| F3 | 0 | 4 (1) | 3 | 3 | 4 (1) | 3 | 17 (2) |
| F4 | 0 | 3 | 3 | 3 | 3 | 3 | 15 |
| NA | 15 | 3 (3) | 0 | 1 (1) | 0 | 0 | 19 (4) |
| Total number of animals replaced | 0 | 4 | 0 | 1 | 1 | 3 | 9 |
| Total number of animals included in the pharmacokinetic analyses | 0 | 12 | 12 | 12 | 12 | 12 | 84 60 |

F1: DSPC/Chol 0.1 D:L ratio Ls-TPT at 0.5 mg/mL + Ls-GD at 1.15 mg/mL
F2: DSPC/DSPG/Chol 0.3 D:L ratio Ls-TPT at 0.5 mg/mL + Ls-GD at 1.15 mg/mL
F3: DSPC/DSPG/Chol 0.1 D:L ratio Ls-TPT at 0.5 mg/mL + Ls-GD at 1.15 mg/mL
F4: Free topotecan at 0.5 mg/mL
DSPC/DSPG = distearoylphosphatidylcholine/distearoylphosphatidylglycerol
Chol = cholesterol
D:L ratio = drug:lipid ratio (w/w)
Ls-TPT = liposomal topotecan
Ls-GD = liposomal gadodiamide
( ) indicates number of animals that were replaced Example 2.2.3

Brain Tissue Concentrations

Topotecan brain tissue concentrations were measurable at 1 and 6 hours only in the free topotecan group (formulation 4). In contrast, measurable brain tissue concentrations were found through 48 hours (formulation 1) or even 96 hours (formulations 2 and 3) in the Ls-TPT groups. None of the formulations had detectable levels at 7 days. At all time points, formulation 2 had the highest tissue concentrations, except at 96 hours where formulations 2 and 3 had very low and similar concentrations. The topotecan levels detected are assumed to reflect encapsulated topotecan for liposomal formulations 1, 2 and 3, particularly beyond 6 hours, given the short half life of free topotecan. Table 4 summarizes the brain tissue concentrations of topotecan by formulation and time point.

TABLE 4

Topotecan Brain Tissue Concentrations by Formulation and Time Point

| Formulation | | 1 hour | 6 hours | 48 hours | 96 hours | 168 hours |
|---|---|---|---|---|---|---|
| F1 | Mean (mg/g of brain tissue) ± STD | 0.0394 ± 0.0073 | 0.0150 ± 0.0115 | 0.0049 ± 0.0036 | 0 | 0 |
| | Mean μM ± STD | 86.06 ± 16.01 | 32.85 ± 25.20 | 10.76 ± 7.90 | 0 | 0 |
| F2 | Mean (mg/g of brain tissue) ± STD | 0.0670 ± 0.0329 | 0.0498 ± 0.0200 | 0.0143 ± 0.0095 | 0.0006 ± 0.0007 | 0 |
| | Mean μM ± STD | 146.40 ± 71.78 | 108.77 ± 43.76 | 31.25 ± 20.77 | 1.24 ± 1.45 | 0 |
| F3 | Mean (mg/g of brain tissue) ± STD | 0.0270 ± 0.0213 | 0.0170 ± 0.0116 | 0.0122 ± 0.0085 | 0.0003 ± 0 | 0 |
| | Mean μM ± STD | 58.90 ± 46.58 | 37.06 ± 25.25 | 26.64 ± 18.65 | 0.70 ± 0 | 0 |
| F4 | Mean (mg/g of brain tissue) ± STD | 0.0203 ± 0.0181 | 0.0071 ± 0.0063 | 0 | 0 | 0 |
| | Mean μM ± STD | 44.29 ± 39.41 | 15.57 ± 13.80 | 0 | 0 | 0 |

F1: DSPC/Chol 0.1 D:L ratio Ls-TPT at 0.5 mg/mL + Ls-GD at 1.15 mg/mL
F2: DSPC/DSPG/Chol 0.3 D:L ratio Ls-TPT at 0.5 mg/mL + Ls-GD at 1.15 mg/mL
F3: DSPC/DSPG/Chol 0.1 D:L ratio Ls-TPT at 0.5 mg/mL + Ls-GD at 1.15 mg/mL
F4: Free topotecan 0.5 mg/mL
DSPC/DSPG = distearoylphosphatidylcholine/distearoylphosphatidylglycerol
Chol = cholesterol
D:L ratio = drug:lipid ratio (w/w)
Ls-TPT = liposomal topotecan
Ls-GD = liposomal gadodiamide Example 2.2.4

Concentration-Time Variables

Figure 2:
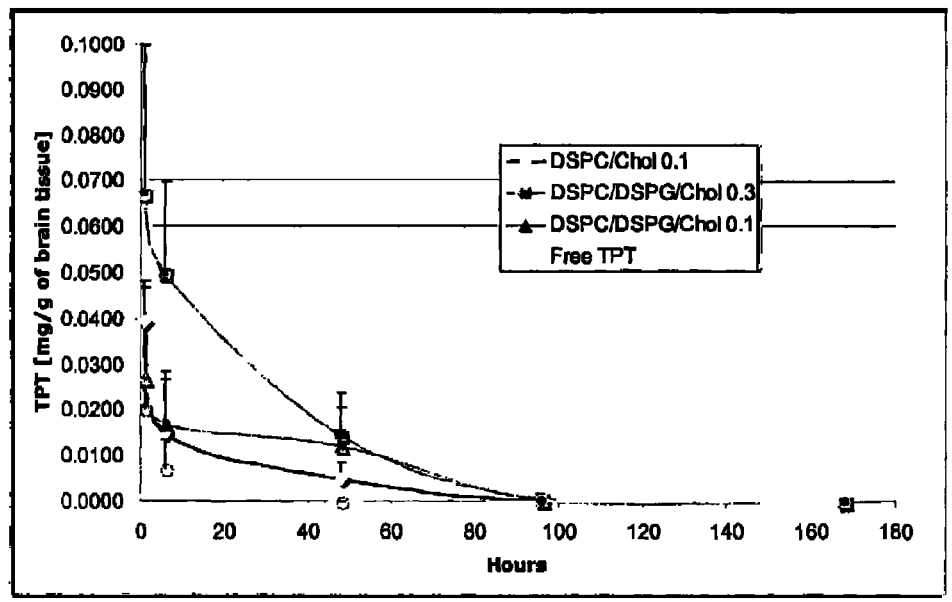
FIG. 2 shows the pharmacokinetics of Ls-TPT Formulations and free topotecan in Normal brain tissue.

As shown in FIG. 2, the highest brain tissue concentrations were achieved with the DSPC/DSPG/Chol 0.3 D:L ratio nanoliposomal formulation of topotecan, while the other two liposomal formulations performed similarly to free topotecan. A brain tissue concentration range of 1.24-146.4 µM over the first 96 hours was determined for the DSPC/DSPG/Chol 0.3 D:L ratio nanoliposomal formulation. The pharmacokinetic (PK) parameters are listed in Table 5 including tissue t1/2 of the drug for each formulation, CL, MRT in the brain, and AUC. Interpretation of PK parameters are taken cautiously as there are insufficient concentration points (at least 3 concentrations in terminal slope) to adequately calculate the regression (WinNonlin Analysis, separate attachment). Due to the limited number of data points (each data point required sacrificing 3 animals), meaningful PK variables could not be calculated with the exception of AUC. The AUC(0-last) was markedly larger for the DSPC/DSPG/Chol 0.3 D:L ratio formulation (153.8 µg·day/g) compared to DSPC/Chol 0.1 and DSPC/DSPG/Chol 0.1 (38.27 and 68.21 µg·day/g, respectively), and free topotecan (5.5 µg·day/g). All the nanoliposomal formulations yielded half-lives in the range of one day while the half-life of free topotecan was much shorter. Based on these results, the Ls-TPT formulation 2 (DSPC/DSPG/Chol 0.3 D:L ratio) was selected for further study.

TABLE 5

Pharmacokinetics of Ls-TPT Formulations and Free Topotecan in Normal Brain Tissue

| Formulation | $t_{1/2}$ (day) | $AUC_{(0\text{-}last)}$ (µg · day/g) | CL (g/day) | $MRT_{inf}$ (day) |
|---|---|---|---|---|
| DSPC/Chol 0.1 D:L ratio nLs-TPT | 1.130 | 38.167 | 0.144 | 1.624 |
| DSPC/DSPG/Chol 0.3 D:L ratio nLs-TPT | 0.852 | 153.791 | 0.072 | 1.063 |
| DSPC/DSPG/Chol 0.1 D:L ratio nLs-TPT | 1.117 | 68.208 | 0.096 | 1.583 |
| Free topotecan | not available* | 5.5 | not available* | not available* |

*Insufficient concentration points to adequately calculate the regression.

Example 2.3

Discussion

The study provided in this Example 2 evaluated the pharmacokinetic profiles in rat normal brain tissue of a combined drug delivery approach comparing 3 novel Ls-TPT formulations and free topotecan delivered via intracerebral CED. Among the 3 nanoliposomal formulations assessed, formulation 2, DSPC/DSPG/Chol with drug to lipid ratio of 0.3 and a topotecan concentration of 0.5 mg/mL, was determined to result in the most optimal intracerebral pharmacokinetic profile with an AUC(0-last) of 153.8 µg·day/g and a half-life of approximately one day. The AUC and half-life of Ls-TPT formulation 2 (DSPC/DSPG/Chol 0.3 D:L ratio) far exceeded that of free topotecan indicating longer drug release kinetics from the liposome, a desirable characteristic for CED delivery. The better pharmacokinetic profile observed for Ls-TPT formulation 2 is likely related to better drug release characteristics with slower release from liposomes of the active drug.

To put the pharmacokinetic profile of Ls-TPT formulation 2 in perspective, the concentrations of topotecan found in our study were compared with data from previous in vitro studies. The concentrations at 6, 48 and 96 hours (108.8, 31.25 and 1.24 µM respectively) were well above the 50% inhibitory concentrations (IC50) of 2.4, 0.038, 0.28 and 0.02->4 µM after exposure over 1, 24, 72 and 120 hours, respectively, of various malignant glioma cells lines (Marchesini 1996, Pollina 1998, Schmidt 2001). Hence, there is a solid basis to assume that Ls-TPT formulation 2 provides for sufficient cytotoxic tissue concentrations of topotecan over at least 96 hours in vivo.

Example 2.4

Conclusions

The Ls-TPT formulation DSPC/DSPG/Chol with drug to lipid ratio of 0.3 and a topotecan concentration of 0.5 mg/mL was determined to result in the most optimal intracerebral pharmacokinetic profile.

Example 3

Convectability of Rhodamine Liposomes Delivered to the Striata of Nude Rats by CED Example 3.1

Materials and Methods

Nine rats were used in this study. Rhodamine liposomes (DSPC/DSPG/Chol, 70:20:10 mole ratio) with 0.5 mole % rhodamine PE were delivered bilaterally to the rat striatum by CED infusion. Dilutions of rhodamine liposomes were prepared using histidine/saline buffer and added sucrose to achieve final sucrose concentrations of 3 mM 15 mM and 5 mM according to Table 7.

TABLE 7

| rhodamine liposomes (uL) | saline (uL) | sucrose (uL) | final sucros | final vol |
|---|---|---|---|---|
| 300 | 96 | 4 | 3 mM | 400 |
| 300 | 80 | 20 | 15 mM | 400 |
| 300 | 0 | 100 | 75 mM | 400 |

For CED, a silicon cannula was connected to the automated pump used for convection-enhanced delivery and was lowered to the appropriate ventral coordinates (AP=+0.5 mm; ML=3.0 mm; DV=−4.5 to −5 mm with the tooth bar at −3.3 mm). The test article was injected bilaterally at one site into each striatum. The infusion rates used in this study to achieve a 20 μL dose per hemisphere were 0.2 μL/min (15 min)+0.5 μL/min (10 min)+0.8 μL/min (15 min). Rats were sacrificed immediately following CED delivery. The brains were removed and divided into left and right hemispheres. Right hemispheres were frozen at −60° C. in dry ice/isopentane and stored at −80° C. for 24 h prior to histological analysis. The left hemispheres of each animal were frozen at −80° C. for subsequent analysis by Northern Lipids, Inc. In some of the rats, the striatum was removed from the left hemisphere for analysis.

TABLE 8

| RAT ID | Vd (mm3) | final sucrose concentration (mM) | vol infused (uL) |
|---|---|---|---|
| 8213 | 17.6 | 3 | 40 |
| 8219 | 13.3 | 15 | 40 |
| 8237 | 33.9 | 15 | 40 |
| 8206 | 13.4 | 3 | 20 |
| 8216 | 11.7 | 3 | 20 |
| 8233 | 23.3 | 15 | 20 |
| 8242 | 26.6 | 15 | 20 |
| 8205 | 12.8 | 75 | 20 |

Rhodamine fluorescence was detected in all rats receiving CED regardless of sucrose concentration with both 40 uL and the 20 uL infusion volumes (Table 9). The mean volumes of distribution ranged from 12.6 mm3 to 24.9 mm$^3$ in all groups.

TABLE 9

| vol rhodamine lipsomes infused (uL/hemisphere) | final sucrose concentration (mM) | Vd rhodamine fluorescence (mm3) | SD | SE | N |
|---|---|---|---|---|---|
| 40 | 3 | 17.6 | na | na | 1 |
| 40 | 15 | 23.6 | 14.56639969 | 10.33077992 | 2 |
| 20 | 3 | 12.55 | 1.202081528 | 0.852540091 | 2 |
| 20 | 15 | 24.95 | 2.333452378 | 1.654930764 | 2 |
| 20 | 75 | 12.8 | na | na | 1 |

The right hemispheres of each rat were sectioned at 20 microns and every 10th section through the striatum was mounted onto slides. Sections were photographed and NIH Image was used to calculate the volume of distribution within the striatum. Rhodamine fluorescence occurring outside of the striatum was not included in the analysis. Histological slides were sent to UCSF for Vd analysis. Tissues obtained from the left hemispheres of each rat will be sent to Northern Lipids for determination of extraction efficiency.

Example 3.2

Results

Rhodamine fluorescence was detected in all rats receiving CED infusions. In all rats, the label distributed within the striatum. Some rats showed strong labeling in the corpus callosum and the internal capsule fiber tracks (data not shown). Table 8 indicates the volume of distribution (Vd) for individual rats at the sucrose concentrations of 3 mM, 15 mM and 75 mM. Due to technical difficulty with the CED tubing, three rats were bilaterally infused with 40 uL of rhodamine liposomes into each striatum (shaded area) rather than 20 uL into each striatum. These rats were not included in the analysis. One animal in the 75 mM group died during surgery (at 5 min) and was not included. Infusion was continued on this animal, however, the liposomes were extruded from the site following the animal's death and did not distribute into the parenchyma.

Figure 3:
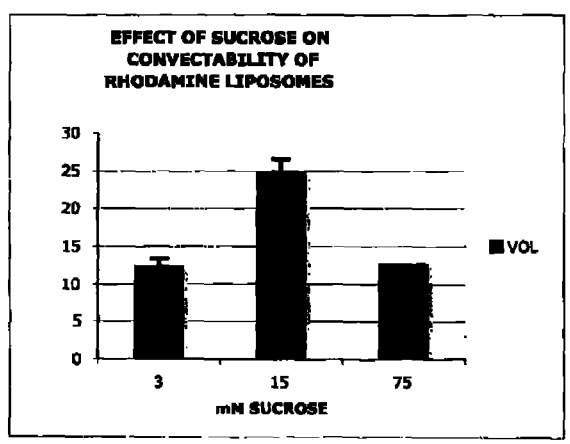
FIG. 3 shows the effect of sucrose on convectability of rhodamine liposomes.

The 15 mM final sucrose concentration demonstrated a two-fold greater volume of distribution compared to the 3 mM final sucrose concentration (FIG. 3). Statistical comparison of the sucrose concentration groups was not determined in this study due to small group size.

The data demonstrate that varying sucrose concentrations in a liposomal preparation does not affect the ability of CED to distribute liposomes to the rat parenchyma. The number of samples in this study was not sufficient perform statistical analysis of the effect of different sucrose concentrations on the volume of distribution following CED delivery of rhodamine liposomes to the rat striatum.

Previous data (FIG. 4) using rhodamine loaded liposomes of varying lipid compositions demonstrated distribution volumes similar to the range obtained in the present study.

In the present study, the volumes of distribution ranged from 11.7 mm$^3$ to 26.6 mm$^3$ among rats receiving 20 μL liposomes per hemisphere at all sucrose concentrations. The data shown in FIG. 4 demonstrate Vds in similar ranges for formulations 1 and 6. Although none of the liposomal formulations in FIG. 4 were identical to the formulation used in the present study, the data suggest a high degree of variability in the procedure that is likely to be related to technical aspects of the infusion procedure. Moreover, the distribution of liposomes to adjacent structures and fiber tracts close to the striatum in rat may account for the within group differences noted in both studies, since distribution of liposomes outside of the striatal region was not included in the Vd calculations.

TABLE 10

Figure 4:
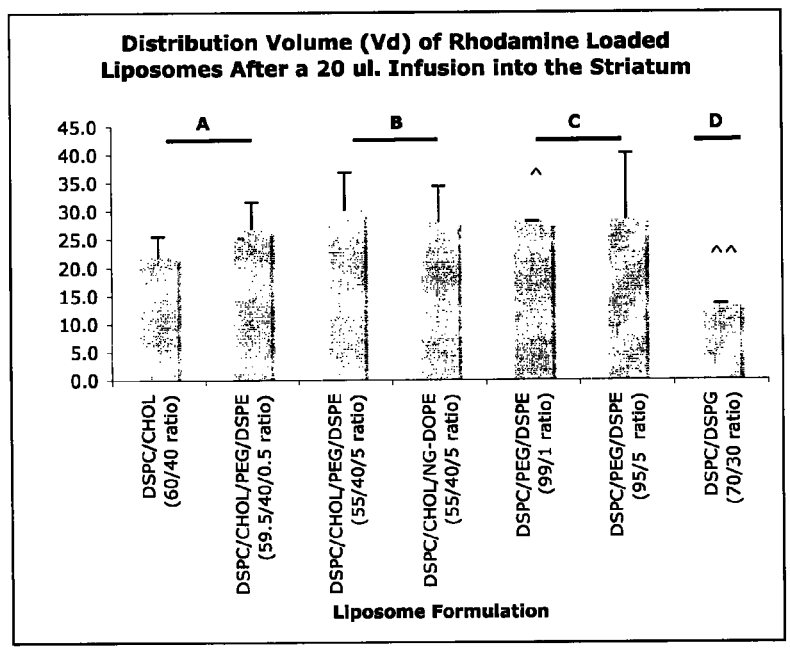
FIG. 4 shows the distribution volume (Vd) of rhodamine loaded liposomes after a 20 μl infusion into the striatum.

Distribution Volume of Various Formulations (see FIG. 4)

| Formulation | 1 left | 2 right | | 3 left | 4 right | | 5 left | 6 right | | 7 left |
|---|---|---|---|---|---|---|---|---|---|---|
| #1: | 23.5 | 19.7 | #2: | na | 21.3 | #8: | na | 11.6 | #7: | na |
| #3: | 16.4 | 31.7 | #4: | 23.9 | 25.6 | #10: | na | 43.5 | #9: | na |
| #5: | 26.1 | 29.6 | #6: | 36.8 | 37.9 | #12: | 28.2 | 31.2 | #11: | 16.8 |
| average | 22.0 | 27.0 | | 30.3 | 28.3 | | 28.2 | 28.8 | | 16.8 |
| sd | 5.0 | 6.5 | | 9.1 | 8.6 | | na | 16.1 | | na |
| sem | 3.6 | 4.6 | | 6.5 | 6.1 | | na | 11.5 | | na |

This data is plotted in FIG. 4. The numbers in the top row correspond to bars 1-7 in FIG. 4, respectively. Individual animals are represented as "#1-12". The actual values represent the distribution volumes obtained with the different formulations.

Example 4

Pharmacological Assessment of Nanoliposomal Compounds Delivered Intracerebrally to the Naïve Rodent Brain and Efficacy of Nanoliposomal Compounds Delivered to Intracranial Xenografted Tumors in the Adult Athymic Rat

Example 4.1

Materials

Example 4.1.1

Test Articles

GLP grade material of both Ls-TPT and Ls-GD were prepared as indicated in Examples 1.1 and 1.2.

Example 4.1.2

Animals and Grouping

Adult male athymic rats rnu/rnu (Charles River Laboratories, Wilmington, Mass., batch 5226156/032607) 6-8 weeks of age weighing 200-300 g were used. The animals were divided in 4 groups as outlined in Table 11.

TABLE 11

Group Assignments and Dosing

| Group | Planned number of animals | Treatment time points | Number of treatments (CED) | Sacrifice time points |
|---|---|---|---|---|
| 1 | 8 | Day 8 | 1 | life span or Day 60 |
| 2 | 8 | Day 8, Day 12 | 2 | life span or Day 60 |
| 3 | 8 | Day 8, Day 12 | 2 | life span or Day 60 |
| 4 | 8 | — | 0 | life span or Day 60 |

Group 1: DSPC/DSPG/Chol D:L 0.3 Ls-TPT at 0.5 mg/mL + Ls-GD at 1.15 mg/mL
Group 2: DSPC/DSPG/Chol D:L 0.3 Ls-TPT at 0.5 mg/mL + Ls-GD at 1.15 mg/mL
Group 3: DSPC/DSPG/Chol D:L 0.3 Ls-TPT at 0.1 mg/mL + Ls-GD at 1.15 mg/mL
Group 4: Control (no surgical procedure or CED)
DSPC/DSPG = distearoylphosphatidylcholine/distearoylphosphatidylglycerol
Chol = cholesterol
D:L ratio = drug to lipid ratio (w/w)
Ls-TPT = liposomal topotecan
Ls-GD = liposomal gadodiamide Rats were assigned to groups based on body weight in a manner to achieve comparable group mean body weights and standard deviations. The groups were then randomly assigned to treatment regimen. Single treatment was planned 8 days post tumor implantation and dual treatment at 8 and 12 days post tumor implantation.

Example 4.1.3

Surgical Procedures and Treatment

Example 4.1.3.1

Intracranial Tumor Xenograft Implantation

Implantation of U87MG tumor cells (human glioblastoma cells; Perry Scientific Inc, San Diego, Calif., lot W5051507U87MC) was performed unilaterally in the right striatum using standard stereotaxic procedures. Rats were anesthetized with isoflurane (2.5%) and the skin over the cranium was shaved. The rat was mounted in a stereotaxic frame with the head positioned by the use of ear bars and the incisor bar. Aseptic techniques were used for all surgical procedures. The skin was disinfected with Betadine solution. A longitudinal incision was performed in the skin on top of the skull and blunt dissection was used to remove connective tissue overlying the skull. A small dental drill was used to drill a burr hole burr hole 0.5 mm anterior and 3.0 mm lateral from the bregma. Using a 30 gauge 25 µL Hamilton syringe, U87MG cells were stereotactically injected into the striatum using the appropriate dorso-ventral coordinates from pial surface (−4.5 to −5 mm with the tooth bar at −3.3 mm). A total volume of 10 µL containing approximately $5.0 \times 10^5$ cells total was injected in the right striatum over a period of 10 minutes. The tumor implantation was done on 2 different days because the number of animals planned did not allow performing all interventions on one single day. Therefore, 2 separate tumor suspensions were prepared.

Following inoculation, the skin was stapled. The rats were monitored during anesthesia recovery. Buprenorphine was administered subcutaneously (SC) before the end of the procedure then buprenorphine was administered SC on an as needed basis. Rats were monitored twice daily following tumor cell implantation. The survival time following implantation was expected to be approximately 0-60 days, wherein the animal was euthanized and the brain harvested.

Example 4.1.3.2

Treatment

Anesthesia was performed with isoflurane (2.5%). A stereotactic frame with blunt ear bars was used to perform CED through the previously performed burr hole. Only the blood clots were removed. Doses were administered via CED using a cannula placed at the tumor implantation site in the right striatum. A fused silica cannula (OD 168 μm, ID 102 μm) (PolyMicro Technologies, Phoenix, Ariz.) connected to an automated pump (BASi, Inc., West Lafayette, Ind.) was used and was lowered to the appropriate dorso-ventral coordinates (−4.5 to −5 mm with the tooth bar at −3.3 mm). Dorso-ventral coordinates were calculated from the pial surface. The cannula was inserted into a 27-gauge needle and secured with superglue on the tubing. The animals were to receive one dose (20 μL) of the Ls-TPT/Ls-GD formulation. A progressive infusion rate increment was used. The infusion rates to be used to administer the 20 μL volume were 0.2 μL/min for 15 min, 0.5 μL/min for 10 min and 0.8 μL/min for 15 min. Following infusion completion the cannula was left in place for 5 minutes to minimize outflow of infusate, and then slowly withdrawn.

Following completion of the procedure, the rats were maintained in a draft free environment, and kept warm via heating lamp or water bottle or other appropriate warming methods and monitored during anesthesia recovery. Buprenorphine was administered subcutaneously on an as needed basis. Rats were allowed to recover in the procedure room prior to return to their home cages.

Example 4.1.4

Euthanasia Criteria Before Day 60

If any one or a combination of symptoms (nasal/periorbital bleeding, paresis, hunching, inactivity or not feeding or grooming or weight loss >15% of baseline body weight) was observed, animals were treated with analgesics. In addition to buprenorphine, an NSAID such as Meloxicam or Ketorolac also was given. In the event the animals did not show signs of improvement within 48 hours they were euthanized as outlined in Example 4.1.5.

Example 4.1.5

Tissue Collection and Processing

At the end of their respective survival period or at 60 days, animals were anesthetized with isoflurane (2.5%) inhalation and then to undergo intracardiac perfusion with PBS followed by 4% paraformaldehyde.

A complete gross necropsy of all animals found dead or sacrificed (scheduled and unscheduled) during the study was performed on the carcass and muscular/skeletal system, all external surfaces and orifices, cranial cavity and external surface of the brain, neck with associated organs and tissues, thoracic, abdominal and pelvic cavities with their associated organs and tissues.

Major organs were collected and stored in formalin 10%. Brains were removed and placed in 4% paraformaldehyde overnight and then equilibrated in 30% sucrose. Brains were then to be frozen and stored at −70° C.

Example 4.1.6

In-Life Observations and Measurements

Clinical observations and measurements were performed at least once daily throughout the acclimation and study period. The clinical observations and measurements are outlined in Table 12.

TABLE 12

Clinical Observations and Measurements

| Monitoring Parameters | Frequency |
| --- | --- |
| Activity | Twice daily Monday through Friday. Weekends and holidays if necessary |
| Excreta | Twice daily Monday through Friday. Weekends and holidays if necessary |
| Appearance | Twice daily Monday through Friday. Weekends and holidays if necessary |
| Grooming | Twice daily Monday through Friday. Weekends and holidays if necessary |
| Posture | Twice daily Monday through Friday. Weekends and holidays if necessary |
| Weight | Twice weekly (following intracranial tumor implantation) and one terminal unfasted body weight prior to necropsy |
| Food Consumption | Weekly |
| Behavior | Twice daily Monday through Friday. Weekends and holidays if necessary |

Example 4.1.7

Early Death/Unsubscribed Sacrifice

If an animal died on study, the time of death was estimated as closely as possible and recorded, and necropsy was performed as soon as possible. If the necropsy could not be performed immediately, the animal was refrigerated (not frozen) to minimize tissue autolysis. The necropsy was performed no later than 12 hours after death.

If an animal appeared in poor condition or in extremis, it could be euthanized. If possible, blood or other specimens were collected and analyzed as appropriate (e.g., for clinical pathology parameters) to help reveal the cause of malaise/morbidity.

Example 4.1.8

Statistical Methods

For survival analysis purposes animals were grouped by treatment arm. In addition, animals in the highest topotecan total dose group (group 2) were compared to all other treatment arms combined including the control group. The latter grouping was also performed within the approximate U87MG cell load groups as described below. Since the number of U87MG cells implanted potentially varied as animals were treated on 2 different days with preparation of 2 separate tumor cell suspensions without pre-implantation cell count, treatment groups were analyzed by tumor cell suspensions and therefore indirectly by approximate U87MG cell load at tumor implantation based on the post-implantation cell count (see Example 4.2.1). The Log-rank test was used to compare survival among the different groups.

Example 4.1.9

Animal Care

Each animal was identified by a numbered ear tag. Additionally, each animal's cage was identified by a cage card listing the animal identification number, study number, group, and sex of the animal.

The animals were housed individually in microisolator cages so they did not disturb each other's wounds. The room(s) in which the animals were kept were documented in the study records. No other species was housed in the same room(s). The rooms were well ventilated (greater than 10 air changes per hour) with 100% fresh air (no air recirculation). A 12-hour light/12-hour dark photoperiod was maintained, except when room lights had to be turned on during the dark cycle to accommodate blood sampling or other study procedures. Room temperature was maintained between 18 and 26° C.

Animals were to have ad libitum access to Prolab RMH 2500, except for periods of fasting. No contaminants were known to be present in the diet at levels that would interfere with the results of this study. Chlorinated, municipal tap water was available ad libitum to each animal via water bottles. Records of annual water quality testing are maintained in the PSI archives. All study animals were acclimatized to their designated housing for at least 3 days prior to study procedures.

Example 4.2

Results

Example 4.2.1

Protocol Deviations

Post-implantation cell counts revealed that the actual numbers of U87MG tumor cells implanted were significantly higher than stipulated by the protocol. Also, the tumor cell density differed markedly between the two suspensions prepared. Specifically, the post-implantation counts for the two suspensions were $6.8 \times 10^5$ and $9.7 \times 10^5$ cells per 10 µL, as compared to the protocol-specified number of $5.0 \times 10^5$. The observed differences are presumably attributable to cell growth between suspension preparation and cell count. Conceivably, the respective pre-implantation counts may therefore have been lower and less different, but it seems unlikely that they were much closer to the protocol-specified number. In order to account for these differences in the analysis of the results, treatment groups were analyzed by approximate U87MG cell load at tumor implantation based on the post-implantation cell count as described in Example 4.1.8.

Four of the tumor implanted animals only had a partial or no gross necropsy as they were found dead in their cage. Three of these animals had only the brain examined while one did not have any organ examined.

Example 4.2.2

Clinical Observations and Measurements

Four animals, two assigned to group 1, one to group 3 and one to group 4 died before tumor implantation probably related to anesthesia performed for the procedure. Within the tumor implanted groups (29 animals), four animals were found dead in their cage during the course of the study. One animal was assigned to group 1, one to group 2 and two to group 4. The 2 animals assigned to group 4 had the high tumor cell load implanted while the others had the low tumor cell load. The other 25 animals were euthanized because they appeared in poor condition, the most common signs being weight loss ≥15% in the great majority of the animals, lethargy, hunched back posture, motor deficits, tremor and laborious breathing.

Example 4.2.3

Efficacy

Eight animals were treated in each group except the control group in which only 5 animals were treated as 4 animals died from anesthesia and the rest of the animals were redistributed across the treatment groups in order to have a total of 8 animals in each active treatment group. Individual survival for each animal and median survival for each treatment group are outlined in Table 13.

TABLE 13

Individual, Treatment Group, and Overall Survival

| Group | Number of animals | Individual survival (days) | Median survival (days) [95% CI] |
|---|---|---|---|
| 1 | 8 | 15, 15, 17, 17, 18, 20, 21, 22 | 17.5 [15-21] |
| 2 | 8 | 15, 16, 18, 19, 23, 24, 24, 25 | 21.0 [16-24] |
| 3 | 8 | 13, 14, 16, 17, 18, 19, 19, 19 | 17.5 [14-19] |
| 4 | 5 | 13, 16, 17, 18, 20 | 17.0 [13-20] |
| Group 1, 3, 4 | 21 | — | 17.0 [16-19] |
| Total | 29 | — | 18.0 [17-19] |

Figure 5:
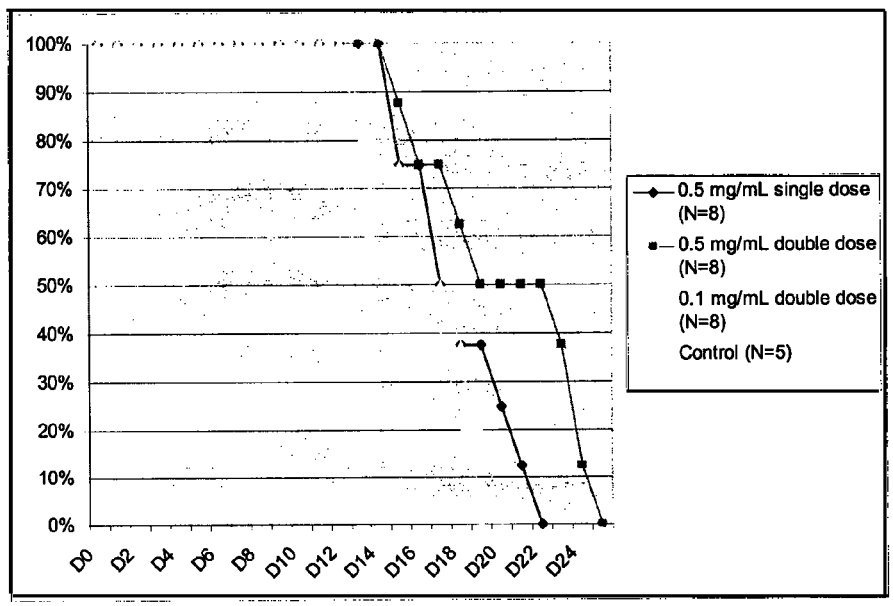
FIG. 5 shows survival of animals by treatment group.

Group 1: DSPC/DSPG/Chol D:L 0.3 Ls-TPT at 0.5 mg/mL + Ls-GD at 1.15 mg/mL
Group 2: DSPC/DSPG/Chol D:L 0.3 Ls-TPT at 0.5 mg/mL + Ls-GD at 1.15 mg/mL
Group 3: DSPC/DSPG/Chol D:L 0.3 Ls-TPT at 0.1 mg/mL + Ls-GD at 1.15 mg/mL
Group 4: Control (no surgical procedure or CED)
DSPC/DSPG = distearoylphosphatidylcholine/distearoylphosphatidylglycerol
Chol = cholesterol
D:L ratio = drug to lipid ratio (w/w)
Ls-TPT = liposomal topotecan
Ls-GD = liposomal gadodiamide Survival by treatment group is shown in FIG. 5 revealing a longer survival for animals treated in group 2 (0.5 mg/mL dual dosing) although not statistically significant by Log-rank test (0.5 mg/mL dual dosing vs. control, p=0.0724; 0.5 mg/mL dual dosing vs. 0.1 mg/mL dual dose, p=0.0593; and 0.5 mg/mL dual dosing vs. 0.5 mg/mL single dose, p=0.0742). Median survival for group 2 was 21 days.

Figure 6:
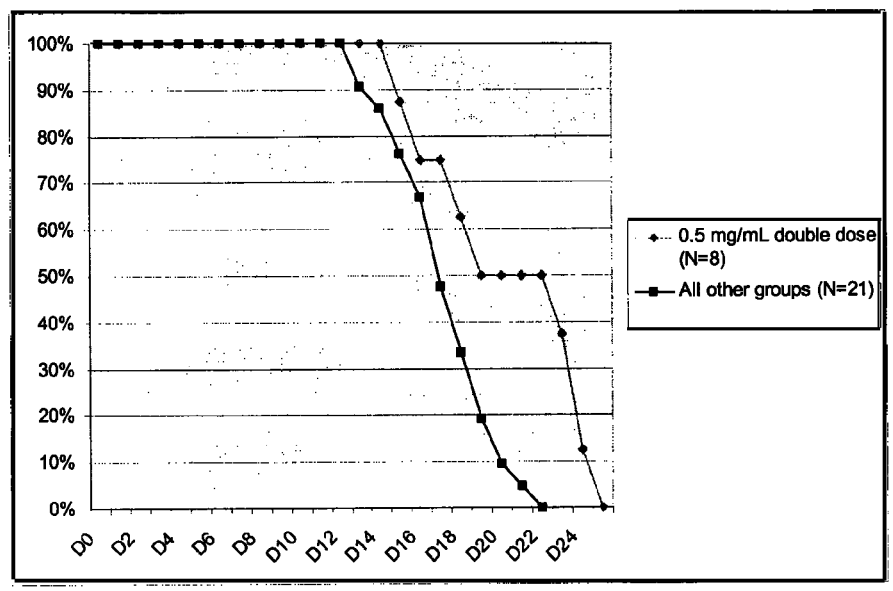
FIG. 6 shows survival of animals by combined treatment group vs. group 2 (0.5 mg/mL dual dosing).

Survival by combined treatment groups (1, 3, 4) compared to group 2 (0.5 mg/mL dual dosing) is shown in FIG. 6. A longer survival for animals treated in group 2 at the highest Ls-TPT total topotecan dose compared to the combined groups is observed which was statistically significant by Log-rank test (p=0.0112). Median survivals of 21 vs 17 days were observed for group 2 and combined group 1, 3 and 4, respectively.

Figure 7:
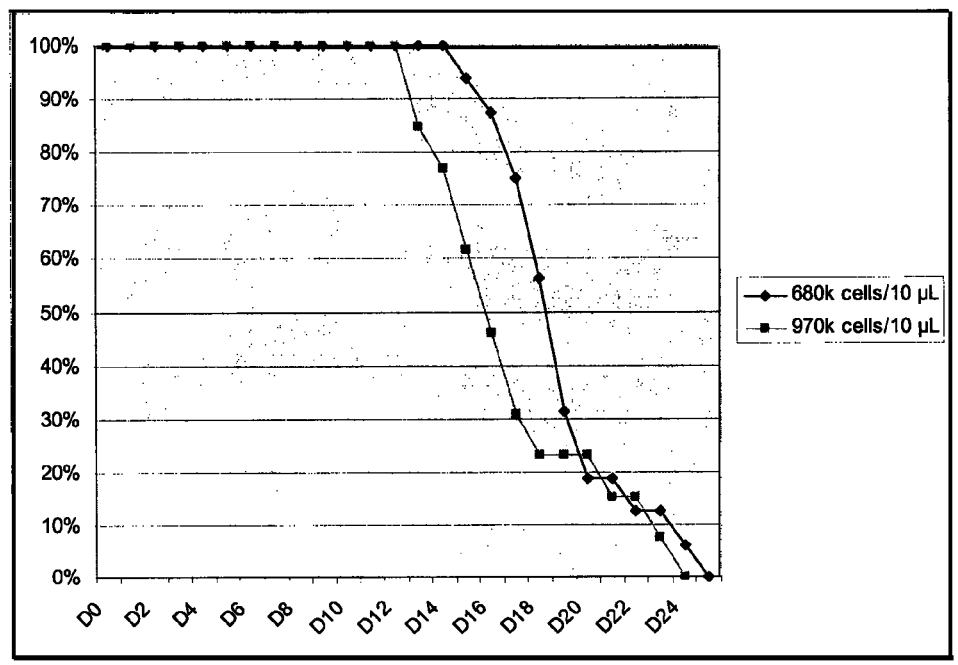
FIG. 7 shows overall survival by U87 cell load at tumor implantation.

Survival (all treatment groups combined) by low ($6.8 \times 10^5$ cells) and high ($9.7 \times 10^5$ cells) U87MG cell load is shown in Table 14 as individual survival for each animal and median survival by implant cell load group, and as overall survival plot in FIG. 7. Survival appears shorter for animals that received a high cell load at tumor implantation with median survival of 16 days versus 19 days for animals that received a low cell load, although (possibly due to small numbers) the survival curves converged towards the end of the survival period.

TABLE 14

Survival by U87MG Cell Load at Tumor Implantation

| Group | Number of animals | Individual survival (days) | Median survival (days) |
|---|---|---|---|
| Low U87MG cell load | 16 | 15, 16, 17, 17, 18, 18 d, 18, 19, 19, 19, 19, 20 d, 20, 22, 24, 24 | 19.0 |
| High U87MG cell load | 13 | 13, 13, 14, 15, 15, 16, 16, 17, 17, 18, 21, 23, 24 | 16.0 |
| Total | 29 | — | 18.0 |

Figure 8:
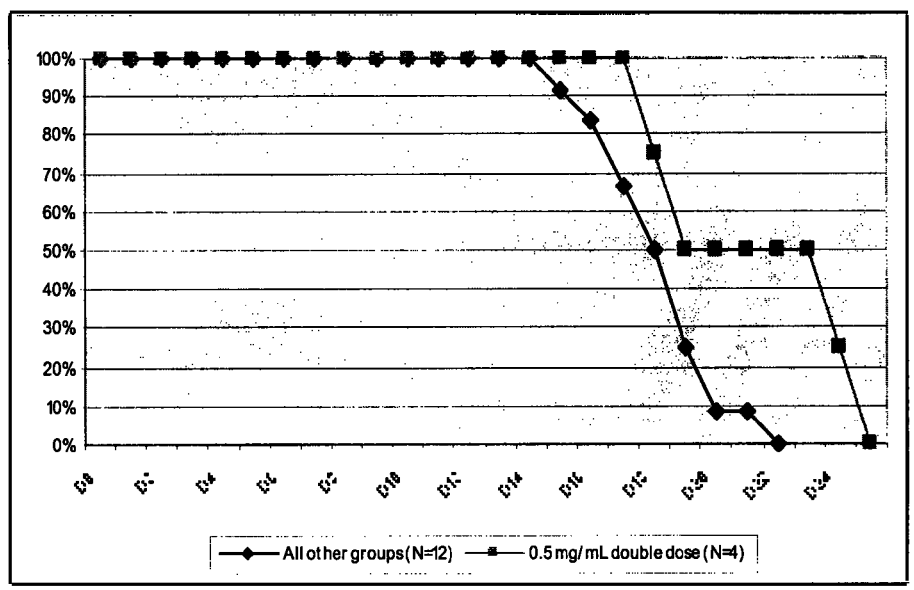
FIG. 8 shows survival of animals by combined treatment groups vs. group 2 (0.5 mg/mL dual dosing) in animals with low U87MG Cell Load ($6.8 \times 10^3$).

Survival by combined treatment groups (1, 3, 4) compared to group 2 (0.5 mg/mL dual dosing) in animals with low U87MG cell load (6.8×10$^5$ cells) is shown in FIG. 8. A longer survival for animals treated in group 2 at the highest Ls-TPT total topotecan dose compared to the combined groups is observed although not statistically significant by Log-rank test (p=0.0646).

Figure 9:
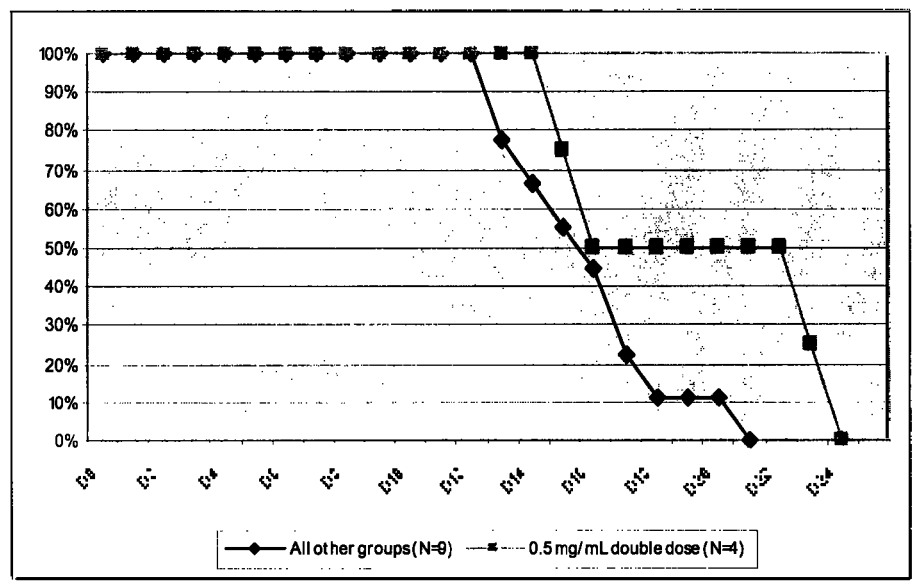
FIG. 9 shows survival of animal by combined treatment groups vs. group 2 (0.5 mg/mL dosing) in animals with high U87MG cell load ($9.7 \times 10^5$)

Survival by combined treatment groups (1, 3, 4) compared to group 2 (0.5 mg/mL dual dosing) in animals with high U87MG cell load (9.7×10$^5$ cells) is shown in FIG. 9. Again, a longer survival for animals treated in group 2 at the highest Ls-TPT total topotecan dose compared to the combined groups is observed although not statistically significant by Log-rank test (p=0.1176).

Example 4.3

Discussion

The studies disclosed in Example 4 evaluated the efficacy of a combined drug delivery approach using a novel Ls-TPT formulation delivered to an intracranial glioma xenograft model in athymic rats by intracerebral CED. This example used 2 dose levels: one previously reported safe by another group, 0.5 mg/mL (Saito 2006), and a lower one at 0.1 mg/mL. In addition, 2 dosing regimens were assessed: single dosing for 0.5 mg/mL and dual dosing 4 days apart for both dose levels studied as only single dosing has been studied thus far. Longer overall and median survivals were observed for the highest Ls-TPT total topotecan dose (0.5 mg/mL dual dosing) compared to the other groups, individually (not statistically significant) or combined (statistically significant). A dose dependent effect was also observed when comparing total dose accounting for dose levels and number of dosing.

Example 4.4

Conclusions

The results of this exploratory efficacy study in a rat glioma model using U87MG suggest that Ls-TPT administered by CED results in survival advantage at the highest dose level assessed (0.5 mg/mL dual dosing).

Example 5

Cytotoxicity of Topotecan and Liposomal Topotecan on U87MG Cells

Example 5.1

Materials and Methods

Example 5.1.1

Test Articles

Free topotecan formulations were obtained from GlaxoSmithKline (Research Triangle Park, N.C.) and Hisun Pharmaceuticals (Taizhou City, Zhejiang, China).

Topotecan for GLP-grade Ls-TPT formulation preparation was obtained from Hisun Pharmaceuticals (Taizhou City, Zhejiang, China). In brief, liposomes were composed of distearoylphosphatidylcholine (DSPC), distearoylphosphatidylglycerol (DSPG) and cholesterol at a 7:2:1 molar ratio with 75 to 90 nm target size. Topotecan was remotely loaded (actively encapsulated) into liposomes in response to a transmembrane pH gradient using internal and external buffers consisting of ammonium sulfate 250 mM pH 5.5 and histidine 10 mM/NaCl 145 mM pH 6.0 respectively. A topotecan concentration of 2.0 mg/mL and a 0.3 (w/w) drug:lipid ratio were targeted assuming a 90-95% drug encapsulation efficiency.

Gadodiamide for Ls-GD preparation was obtained from was obtained from Estech Pharma, Ansan-Si, Gyeonggi-Do, Korea. GLP-grade Ls-GD was prepared similarly topoCED, except that the GD was passively encapsulated in the nanoliposomes. Following removal of un-encapsulated GD and solvents by diafiltration, the final GD encapsulation was ≥90%. The target GD content was 5.0 mg/mL±10% and a particle size range of 75 to 120 nm.

Test articles of Ls-TPT were stored frozen (−20 to −30° C.) and Ls-GD were stored refrigerated (2 to 8° C.), respectively, and protected from light. Test article solutions were prepared fresh on the day of dosing and kept at room temperature. Appropriate dilutions of the test article stock solution with 5 mM histidine, 145 mM NaCl pH 6.0, 300 mM sucrose or 0.9% saline were performed to yield test solutions at appropriate concentrations at the desired test volumes.

Example 5.1.2

Cell Line and Culture

U87MG human glioblastoma cell line was used for all experiments (UCSF culture facility, San Francisco, Calif.). The cells were established in T175 Falcon flasks (BD Bioscience, San Jose, Calif.). The cells were maintained in complete minimal essential medium (CMEM), consisting of Eagle's minimal essential medium (MEM) supplemented with 10% fetal bovine serum, non-essential amino acids and antibiotics (streptomycin 100 μg/mL, penicillin 100 U/mL). All media components were from UCSF cell culture facility. Cultures were incubated at 37° C. in a humidified chamber with 5% CO$_2$. Once a 95% confluence was achieved, cells were trypsinized briefly with 0.05% trypsin-0.02% ethylenediaminetetra-acetic acid (UCSF culture facility, San Francisco, Calif.), and cells were centrifuged at 500×g for 10 minutes. After the supernatant was aspirated, the cells were resuspended directly in 5 ml of a complete cell growth medium (with antibiotics and 10% fetal bovine serum). The cell count was done with trypan blue in a hematocyter (Hausser Scientific, Horsham, Pa.). The appropriate amount of complete cell growth medium was added to achieve a final concentration of 10,000 cells in 100 μL for transfer in each well of 96-well plates designed for luminescence-based cell viability assay (CellTiter-Glo™, Promega, Madison, Wis.). Cells were allowed to attach for 24 hours before any exposure to test article. The culture medium was removed from the 96-well plates just before adding 100 μL of test article using a 12-multichannel pipettor. After exposure to test article, cytotoxic assays were conducted at 24, 48 and 72 hours. All time points of each test article and control were run in triplicates.

Example 5.1.3

Experimental Design

Table 15 outlines the different test article and concentrations evaluated along with controls.

TABLE 15

Test articles and experimental design

| Test Articles | Concentrations (μM) |
|---|---|
| Free TPT (Hisun Pharmaceuticals) | 0.01, 0.1, 1.0, 10 |
| Free TPT (GlaxoSmithKline) | 0.01, 0.1, 1.0, 10 |
| Ls-TPT | 0.01, 0.1, 1.0, 10 |
| Ls-TPT and Ls-GD | 0.01, 0.1, 1.0, 10 (200 for Ls-GD) |
| Ls-GD | 200 |
| Control U87MG in culture medium | — |
| Background control (culture medium only) | — |

TPT = Topotecan
Ls-TPT = liposomal topotecan
Ls-GD = liposomal gadodiamide

All calculations and dilutions of test articles were verified by a second investigator. Test article dilutions were performed with the culture medium used for U87MG culture.

Example 5.1.4

Viability Assay

The assay is based on quantification of the ATP present, as an indicator of metabolically active cells using a thermostable form of luciferease. The luciferase uses luciferin, oxygen and ATP as substrates in a reaction producing oxyluciferin and releasing energy in the form of light. The amount of light produced is proportional to the amount of ATP present, reflecting the number of viable cells. At the pre-determined time points 20 μL of CellTiter-Glo luminescent cell viability assay reagent (Promega, Madison, Wis.) was added to each well used for that time point. After gently agitating the plates, they were put back into the incubator for one hour. The plates' luminescence was then read using an FLx800 Multi-Detection Microplate Reader (Biotek, Winooski, Vt.). The relative light units (RLU) obtained for each well were converted into numbers of viable cells based on a standard curve. Cell survival fractions and IC50 values were derived from graphic extrapolation (Gen 5 Data Analysis Software, Biotek, Winooski, Vt.).

Example 5.1.5

Statistical Methods

All cytotoxic assays were run in triplicate, and mean values are being reported at all concentrations and time points. No other statistics were applied.

Example 5.2

Results

Cytotoxic activity and potency of different sources and formulations of free topotecan (GlaxoSmithKline and Hisun Pharmaceutical) and liposomal topotecan appear very similar at comparable concentrations (0.01, 0.1, 1.0 and 10 μM) and time points (24, 48 and 72 hours) supporting the potential efficacy of Ls-TPT formulations. Ls-GD alone or co-infused with Ls-TPT did not appear to result in cytotoxicity even at the very high concentration of 200 μM and consequently seems a good candidate surrogate imaging tracer for Ls-TPT. (data not shown). The general absence of difference between free topotecan and liposomal topotecan in this study may be explained by the in vitro nature of the environment resulting in a rapid release of the topotecan from the liposomes, with the pharmacokinetic advantages of the liposomal formulations becoming more apparent in vivo.

Example 6

Convection Profile and Tissue Distribution in Normal Brain and Xenografted U87MG Tumors of Different Formulations of Liposomal Topotecan and Liposomal Gadodiamide Administered by Intracerebral Convection-Enhanced Delivery to the Adult Athymic Rat Example 6.1

Example 6.1.1

Test Articles

GLP grade material Ls-TPT and Ls-Gd were prepared as described in Examples 2.1.1 and 2.1.2. Gadodiamide for Ls-GD preparation was obtained from Estech Pharma, Ansan-Si, Gyeonggi-Do, Korea. Ls-GD was prepared similarly topoCED, except that the GD was passively encapsulated in the nanoliposomes. Following removal of un-encapsulated GD and solvents by diafiltration, the final GD encapsulation was ≥90%. The target GD content was 5.0 mg/mL±10% and a particle size range of 75 to 120 nm.

Different fluorophores were used to label Ls-TPT and Ls-GD in order to allow differential microscopic fluorescence/luminescence: marina blue-DHPE (1,2-dehexadecanoyl-sn-glycero-3-phosphoethanolamine) (Invitrogen, Carlsbad, Calif.) for Ls-TPT and rhodamine-PE (phosphoethanolamine) (Invitrogen, Carlsbad, Calif.) for Ls-GD. Marina blue-DHPE and rhodamine-PE labeled liposomes were prepared similarly to Ls-TPT and Ls-GD respectively with the fluorophores added to the lipid powder at the same time as the solvent solution based on a DSPC:DSPG:cholesterol:fluorophore molar ratio of 69.7:20:10:0.3.

Test articles of Ls-TPT were stored frozen (−20 to −30° C.) and Ls-GD were stored refrigerated (2 to 8° C.), respectively, and protected from light. Dosing solutions were prepared fresh on the day of dosing and kept at room temperature.

Appropriate dilutions with 0.9% saline of the test article stock solution were performed to yield the desired concentrations. Fresh vials of the stock test article solutions were used on each dosing day. No control article was used in this study.

Example 6.1.2

Animals and Grouping

Adult male athymic rats rnu/rnu (Taconic, Germantown, N.Y.) (batches 071007 and 073107) 6-8 weeks of age weighing 200-275 g were used. The animals were divided in 4 groups as outlined in Table 16.

TABLE 16

Group Assignments and Dosing

| Group | Drug to lipid ratio (w/w) | Target tissue | Injection volume (µL) | Ls-TPT concentration (mg/mL) | Ls-GD concentration (mg/mL) | Treatment time points | Sacrifice time points | Planned number of animals |
|---|---|---|---|---|---|---|---|---|
| 1 | 0.1 | Naïve brain tissue | 20 bilateral | 0.38 | 1.15 | Day 1 | Day 1 | 3 |
| 2 | 0.3 | Naïve brain tissue | 20 bilateral | 1.02 | 1.15 | Day 1 | Day 1 | 3 |
| 3 | 0.1 | U87MG xenograft | 20 unilateral | 0.38 | 1.15 | Day 10 | Day 10 | 4 |
| 4 | 0.3 | U87MG xenograft | 20 unilateral | 1.02 | 1.15 | Day 10 | Day 10 | 4 |
| Total | — | — | — | — | — | — | — | 14 |

Group 1: Naïve brain tissue - DSPC/DSPG/Chol D:L 0.1 + Ls-TPT 0.38 mg/mL + Ls-GD 1.15 mg/mL
Group 2: Naïve brain tissue - DSPC/DSPG/Chol D:L 0.3 + Ls-TPT 1.02 mg/mL + Ls-GD 1.15 mg/mL
Group 3: Tumor tissue - DSPC/DSPG/Chol D:L 0.1 + Ls-TPT 0.38 mg/mL + Ls-GD 1.15 mg/mL
Group 4: Tumor tissue - DSPC/DSPG/Chol D:L 0.3 + Ls-TPT 1.02 mg/mL + Ls-GD 1.15 mg/mL
DSPC/DSPG = distearoylphosphatidylcholine/distearoylphosphatidylglycerol
Chol = cholesterol
D:L ratio = drug to lipid ratio (w/w)
Ls-TPT = liposomal topotecan
Ls-GD = liposomal gadodiamide At the beginning of the study, rats were assigned to the formulation and tissue groups based on body weights in a manner so as to achieve comparable group mean body weights and standard deviations. Animals in both formulation groups were to receive CED infusions on Day 1 if they were assigned to the naïve brain tissue group, and on Day 10, if they were assigned to the tumor tissue group.

Example 6.1.3

Surgical Procedures and Treatment

Example 6.1.3.1

Intracranial Tumor Xenograft Implantation

This procedure was performed for rats assigned to the tumor tissue groups. Human glioblastoma cells (U87MG) were obtained from frozen cell stock (Perry Scientific Inc, San Diego, Calif.) two weeks prior to the scheduled inoculation. Cells were harvested on the day of tumor inoculation surgery and adjusted to a density of 50,000 to 100,000 cells/µL. On the day of inoculation (Day 0), each rat was implanted with a total of 500,000 U87MG tumor cells unilaterally into the right striatum using 5-10 µL of suspension. A stereotactic technique and anesthesia with isoflurane (2.5%) were used. The rat was mounted in a stereotactic frame with the head positioned by the use of ear bars and an incisor bar. Aseptic techniques were used for all surgical procedures. The skin was disinfected with 70% alcohol followed by betadine solution. A longitudinal incision was made in the skin on top of the skull and blunt dissection was used to remove connective tissue overlying the skull. A burr hole was drilled 0.5 mm anterior and 3.0 mm lateral from the bregma. Using a 30 gauge 25 µL Hamilton syringe, U87MG cells were stereotactically injected into the striatum using the appropriate dorsoventral coordinates from pial surface (−4.5 to −5 mm with the tooth bar at −3.3 mm). Depending on the final cell concentration of the U87MG suspension, the volume of injection was adjusted between 5 and 10 µL to ensure that a total of 500,000±25,000 cells be delivered over a period of 10 minutes.

Following inoculation, the skin was stapled. The rats were monitored during anesthesia recovery. Buprenorphine was administered subcutaneously (SC) before the end of the procedure then buprenorphine was administered SC on an as needed basis.

Example 6.1.3.2

Treatment

The test articles were administered via CED infusion on study Day 1 in rats assigned to the naïve brain tissue groups, and on Day 10 in rats assigned to the tumor tissue groups. Doses were administered via CED bilaterally to the dorsolateral striatum of the rats in the naïve tissue groups, and intratumorally in the rats in the tumor tissue groups using the same coordinates that were used for the tumor implantation. Rats were dosed in a systematic order that distributed the time of dosing similarly across all groups. Anesthesia was performed with either isoflurane (2.5%) or a combination of ketamine (90 mg/kg) and xylazine (12 mg/kg) via an intraperitoneal injection. A stereotactic frame with blunt ear bars was used to perform CED. In rats assigned to the naïve brain tissue groups, bilateral burr holes were created as outlined in section 5.3.1. In rats assigned to the tumor tissue groups, the scalp incision was reopened to visualize the previously prepared burr hole. Only the blood clots were removed. A fused silica cannula (OD 168 µm, ID 102 µm) (PolyMicro Technologies, Phoenix, Ariz.) connected to an automated pump (BASi, Inc., West Lafayette, Ind.) was used for CED and was lowered to the appropriate dorso-ventral coordinates (−4.5 to −5 mm with the tooth bar at −3.3 mm). Dorso-ventral coordinates were calculated from the pial surface. The cannula was inserted into a 27-gauge needle and secured with superglue on the tubing. A progressive infusion rate increment was used. The infusion rates used in this study to achieve a total infusion volume (Vi) of 20 µL per treatment were 0.2 µL/min for 15 min, 0.5 µL/min for 10 min and 0.8 µL/min for 15 min. Following infusion the cannulae were left in place for 5 minutes to avoid infusate outflow, and then slowly withdrawn. Following completion of the procedure, the rats were maintained in a draft free environment, and kept warm via heating lamp or water bottle or other appropriate warming methods and monitored during anesthesia recovery. Buprenorphine was administered subcutaneously on an as needed basis.

Example 6.1.3.3

Euthanasia

One hour following CED infusion of the test articles, on Day 1 (naïve brain tissue groups) or Day 10 (tumor tissue groups) all rats in all groups were euthanized and the brains removed for histological analysis. For euthanization, animals were deeply anesthesized with isofluorane (2.5%) and then undergo intracardiac perfusion with 0.9% saline (100 mL) followed by 4% paraformaldehyde (300 mL).

Example 6.1.3.4

Tissue Collection and Processing

A complete gross necropsy of all animals found dead or sacrificed (scheduled and unscheduled) during the study was performed on the carcass and muscular/skeletal system, all external surfaces and orifices, cranial cavity and external surface of the brain, neck with associated organs and tissues, thoracic, abdominal and pelvic cavities with their associated organs and tissues.

The brain was removed, incubated in 4% paraformaldehyde for up to 24 h, and then equilibrated in 30% sucrose. Following sucrose equilibration, the tissue was frozen at −60° C. in a mixture of dry ice and isopentane and stored at −70° C. for subsequent processing. The heart, lungs, liver, kidneys, spleen (or portions of), when present, were also to be collected and preserved. These tissues were fixed in neutral-buffered 10% formalin. Formalin fixed organs were then to be grossed and processed to paraffin blocks for subsequent histopathological analyses if required.

Example 6.1.3.5

Histopathological Analyses and Volume of Distribution Assessment

Brains were cryosectioned at 20 microns and every fourth section was collected onto glass slides, and cover slipped with Fluoromount-G. The convection profiles and tissue distribution of both Ls-TPT and Ls-GD were determined by means of fluorescence microscopy, the image captured using a SPOT camera, SPOT software and a Macintosh G4 computer, and the volume of distribution (Vd) of both marina blue-DHPE and rhodamine-PE fluorophores in the sections was calculated using Macintosh-based image analysis system [ImageJ, National Institute of Health (NIH), Bethesda, Md.]. Region of interests (ROI) were drawn using NIH image software and distribution data was transferred to an excel spreadsheet. Distribution volumes ($mm^3$) were calculated by multiplying the mean ROI area ($mm^2$) and the distribution distance (mm). Remaining sections were stored at 4° C. and could be used for additional immunohistochemical analyses.

Example 6.1.3.6

In-Life Observations and Measurements

Clinical observations and measurements were performed at least once daily throughout the acclimation and study period. Recording of cage side observations were to commence at least 3 days prior to dosing and were to continue until termination. Each animal was observed for changes in general appearance and behavior.

Example 6.1.3.7

Early Death/Unscheduled Sacrifice

Rats receiving intracerebral injections of U87MG tumor cells typically have a life span of 17-25 days, and they remain asymptomatic until shortly before death. Although unlikely given the early sacrifice at Day 10 in this study, if any one or combination of the symptoms (nasal/periorbital bleeding, paresis, hunching, inactivity or not feeding or grooming or weight loss >15% of baseline body weight) were observed, the animal could be euthanized. If possible, blood or other specimens were collected and analyzed as appropriate (e.g., for clinical pathology parameters) to help reveal the cause of malaise/morbidity.

If an animal died on study, the time of death was estimated as closely as possible and recorded, and necropsy was performed as soon as possible. If the necropsy could not be performed immediately, the animal was refrigerated (not frozen) to minimize tissue autolysis. The necropsy should be performed no later than 12 hours after death.

Example 6.1.3.8

Statistical Methods

Descriptive statistics (mean and standard deviation) were used to summarize the data and present them graphically.

Example 6.1.4

Animal Care

Each animal was identified by a numbered ear tag. Additionally, each animal's cage was identified by a cage card listing the animal identification number, study number, group, source, arrival date, species/strain, date of birth and sex of the animal.

The animals were housed individually in isolator cages. The bedding material was shaved hardwood chips (Sanichips, Harlan, Calif.) and was changed weekly. Room temperature was centrally maintained at 18-26° C. (64-79° F.), with relative humidity at 30-70%. Temperature and humidity were continuously monitored and daily minimums and maximums recorded. A 12-hour light/12-hour dark cycle illumination period was maintained, except when room lights had to be turned on (during the dark cycle) to accommodate study procedures.

The rats were to have ad libitum access to irradiated Teklad Global 18% Protein Rodent Diet (Harlan, San Diego, Calif., USA) and municipal tap water throughout the study period. No contaminants were known to be present in the diet or water at levels that would have a deleterious effect on the results of the study. Records of annual water quality testing are maintained in the PSI archives.

Upon arrival at the designated housing, all rats accepted for receipt following an initial health inspection were allowed to acclimatize to the housing environment (primary enclosure and room) for a minimum of 3 days prior to initiating any animal-related study procedures. During the acclimatization period, the general health of the rats was monitored daily. Only rats that were visually appraised to be in good clinical condition (i.e., within body weight specifications) were enrolled in the study. Any rats that appeared abnormal and exhibited signs of poor health (i.e., ruffled coat, significantly low body weight) were excluded from the study.

Example 6.2

Results

Example 6.2.1

Protocol Deviations

Although animals assigned to the tumor tissue groups had unilateral tumor implantation, CED of test articles was performed bilaterally (in left hemisphere naïve brain tissue and in right hemisphere tumor tissue). Brain specimen section thickness was changed from 20 µm to 30 µm for all animals with every fifth brain section collected instead of every fourth in order to increase the fluorescence signal.

Example 6.2.2

Clinical Observations and Measurements

No animals had to be replaced in this study. No animals were found dead and all had scheduled sacrifice performed. The pre-sacrifice examination was normal in all animals of both naïve brain tissue and tumor tissue groups.

Example 6.2.3

Convection Profiles and Tissue Distribution

Figure 10:
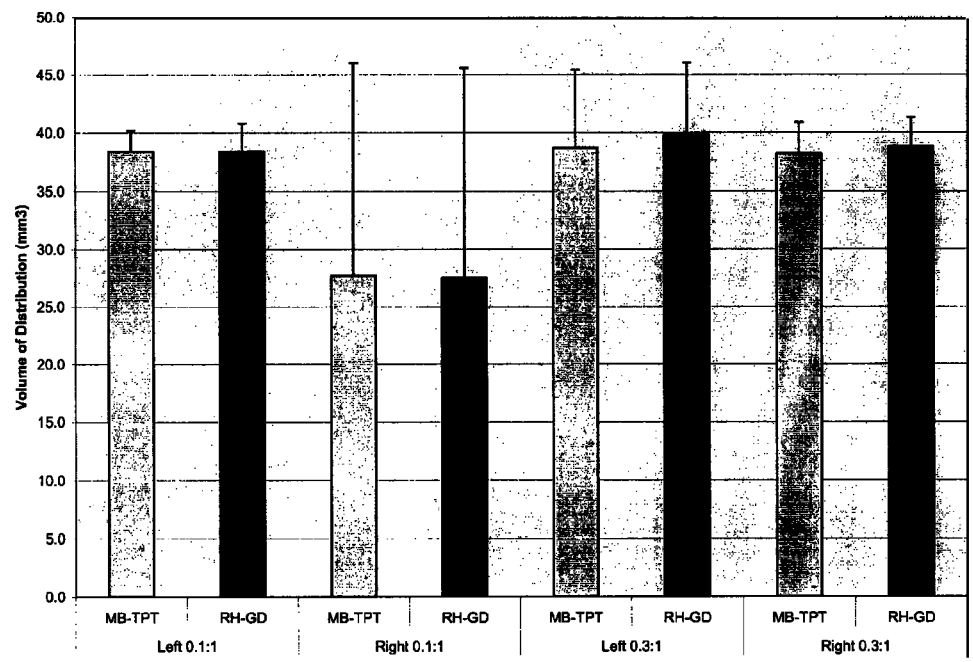
FIG. 10 shows volume of distribution of Ls-TPT-marina blue DHPE coinfused with Ls-Gd-rhodamine-PE in naïve rodent brain tissue. For each formulation, n=3 and 20 μL was infused in each hemisphere.
Figure 11:
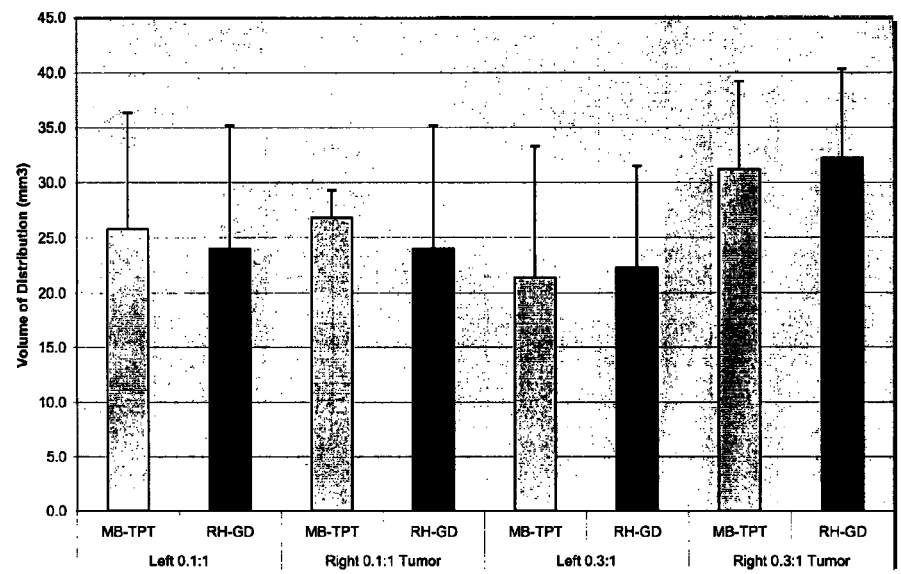
FIG. 11 shows volume of distribution of Ls-TPT-marina blue DHPE coinfused with Ls-Gd-rhodamine-PE in U87MG xenograft rodent brain tissue. For each formulation, n=4 and 20 μL was infused in each hemisphere.

Fourteen animals were treated consistent with the treatment schedule and planned number of animals to be treated in each group. Individual volumes of distribution (Vd) along with means and standard deviations, and the correlation coefficients for the Vd of Ls-TPT-marina blue DHPE and Ls-Gd-rhodamine-PE for groups 1 and 2 (naïve brain tissue) are shown in Table 17 and displayed graphically in FIG. 10, and for groups 3 and 4 (tumor tissue) shown in Table 18 and displayed graphically in FIG. 11. The CORR procedure in Statistical Analysis System (SAS) was used to produce Pearson correlation coefficients.

TABLE 17

Volumes of Distribution of Ls-TPT-marina blue DHPE and Ls-Gd-rhodamine-PE in Naïve Brain Tissue

| Group | Drug to lipid ratio (w/w) | Target tissue | Actual number of animals | Animal ID | Ls-TPT-marina blue DHPE $V_d$ (mm³) Left | Ls-TPT-marina blue DHPE $V_d$ (mm³) Right | Ls-Gd-rhodamine-PE $V_d$ (mm³) Left | Ls-Gd-rhodamine-PE $V_d$ (mm³) Right |
|---|---|---|---|---|---|---|---|---|
| 1 | 0.1:1 | Naïve brain tissue | 3 | 7635 | 38.4 | 43.4 | 40.0 | 44.5 |
|   |   |   |   | 7636 | 36.6 | 37.5 | 35.7 | 35.6 |
|   |   |   |   | 7643 | 40.1 | # | 39.6 | # |
|   |   | Mean ± SD |   |   | 38.4 ± 1.8 | 40.5 ± 4.2 | 38.4 ± 2.4 | 40.1 ± 6.3 |
|   |   |   |   |   |   | 39.0 ± 3.0 |   | 39.0 ± 4.2 |
|   | Correlation Coefficient (TPT and GD distributions) |   |   |   |   |   | 0.95 |   |
| 2 | 0.3:1 | Naïve brain tissue | 3 | 7644 | 47.3 | 40.4 | 47.5 | 38.7 |
|   |   |   |   | 7645 | 30.9 | 34.4 | 32.2 | 35.7 |
|   |   |   |   | 7646 | 38.0 | 39.8 | 39.7 | 41.9 |
|   |   | Mean ± SD |   |   | 38.7 ± 6.7 | 38.2 ± 2.7 | 39.8 ± 6.2 | 38.8 ± 2.5 |
|   |   |   |   |   |   | 38.5 ± 5.6 |   | 39.3 ± 5.3 |
|   | Correlation Coefficient (TPT and GD distributions) |   |   |   |   |   | 0.97 |   |

For animal 7643 on the right hemisphere, no or minimal fluorescence signal was seen with both Ls-TPT and Ls-GD, possibly due to an infusion malfunction or operator error.

Group 1: Naïve brain tissue - DSPC/DSPG/Chol D:L 0.1 + Ls-TPT 0.38 mg/mL + Ls-GD 1.15 mg/mL Group 2: Naïve brain tissue - DSPC/DSPG/Chol D:L 0.3 + Ls-TPT 1.02 mg/mL + Ls-GD 1.15 mg/mL

TABLE 18

Volumes of Distribution of Ls-TPT-marina blue DHPE and Ls-Gd-rhodamine-PE in Tumor Implanted Animals

| Group | Drug to lipid ratio (w/w) | Target tissue | Actual number of animals | Animal ID | Ls-TPT-marina blue DHPE $V_d$ (mm³) Left | Ls-Gd-rhodamine-PE $V_d$ (mm³) Left | Ls-TPT-marina blue DHPE $V_d$ (mm³) Right | Ls-Gd-rhodamine-PE $V_d$ (mm³) Right |
|---|---|---|---|---|---|---|---|---|
| 3 | 0.1:1 | U87MG xenograft* | 4 | 7607 | 14.6 | 13.4 | # | # |
|   |   |   |   | 7613 | 35.6 | 35.8 | 24.7 | 21.6 |
|   |   |   |   | 7630 | 27.3 | 22.9 | 26.1 | 21.5 |
|   |   |   |   | 7633 | # | # | 29.5 | 29.3 |
|   | Mean ± SD |   |   |   | 25.8 ± 10.6 | 24.0 ± 11.2 | 26.8 ± 2.5 | 24.1 ± 4.5 |
|   | Correlation Coefficient (TPT and GD distributions) |   |   |   | 0.98 |   | 0.96 |   |
| 4 | 0.3:1 | U87MG xenograft* | 4 | 7608 | 38.8 | 35.5 | 34.4 | 34.4 |
|   |   |   |   | 7617 | 18.7 | 19.6 | 40.9 | 42.2 |
|   |   |   |   | 7619 | 12.1 | 14.2 | 25.6 | 29.1 |
|   |   |   |   | 7622 | 16.1 | 19.8 | 23.8 | 23.1 |
|   | Mean ± SD |   |   |   | 21.4 ± 11.9 | 22.3 ± 9.2 | 31.2 ± 8.0 | 32.2 ± 8.1 |
|   | Correlation Coefficient (TPT and GD distributions) |   |   |   | 0.99 |   | 0.97 |   |

The Vd values of Ls-TPT-marina blue DHPE for both formulations were in a tight range in the naïve brain tissue groups (means of 39.0±3.0 and 38.5±5.6 mm³ for D:L 0.1:1 and 0.3:1, respectively), with corresponding Vd:Vi ratios of 1.9 2.0. In contrast, the Vd values were markedly smaller and generally more variable in the tumor tissue groups, with means of 25.8 mm³±10.6 and 21.4±11.9 for the two Ls-TPT formulations in naïve brain tissue, and means of 26.8±2.5 and 31.2±8.0 mm³ in tumor tissue. The corresponding Vd:Vi ratios were 1.1-1.3 in naïve brain tissue and 1.3-1.6 in tumor tissue. Although there were minor differences between the two Ls-TPT formulations in the tumor tissue group, these were inconsistent (Vd values with D:L 0.1:1 nominally higher than with D:L 0.3:1 in naïve brain tissue, but nominally lower in tumor tissue) and not statistically significant.

The results for Ls-Gd-rhodamine-PE were remarkably consistent with those for Ls-TPT-marina blue DHPE. Specifically, the mean Vd values were 39.0±4.2 and 39.3±5.3 mm³ in the naïve brain tissue groups, with corresponding Vd:Vi ratios of 1.9-2.0. In the tumor tissue groups, the mean Vd values were 24.0±11.2 and 22.3±9.2 mm³ in naïve brain tissue, and 24.1±4.5 and 32.2±8.1 mm³ in tumor tissue. The corresponding Vd:Vi ratios were 1.1-1.2 in naïve brain tissue and 1.2-1.6 in tumor tissue.

Consistent with the individual distribution results, the correlation between the mean Vd values of Ls-TPT-marina blue DHPE and Ls-Gd-rhodamine-PE was excellent in all treatment groups (range: 0.95 to 0.99), and there were no appreciable differences in the correlation between tissue types (naïve brain vs. tumor tissue).

In three animals all receiving the DSPC/DSPG/Chol D:L 0.1 formulation, there was minimal to no fluorescent signal observed with both Ls-TPT-marina blue DHPE and Ls-Gd-rhodamine-PE in one of the hemispheres. One of these animals was in the naïve brain tissue group (rat #7643), the other two animals were implanted with U87 tumor xenografts (tumor tissue group), and one instance occurred on the tumor xenograft side (rat #7607) while the other instance occurred on the non-implanted side (rat #7633). All instances were possibly due to an infusion malfunction or operator error.

Example 6.3

Discussion

This Example 6 evaluated the convection profile and volumes of distribution of two formulations of a therapeutic nanoliposomal compound, Ls-TPT, and an imaging tracer surrogate for Ls-TPT, Ls-Gd, using different fluorophores to co-label these liposomes in order to demonstrate any differential tissue distribution.

Both topotecan and gadodiamide encapsulated in non-PEGylated DSPC/DSPG/Chol liposomes (7:2:1 molar ratio) convected reliably and consistently in naïve rat brain tissue. The observed Vd:Vi ratios of 1.9-2.0 were consistent with expectations based on previously published data with a PEGylated liposomal formulation (Saito 2004). Importantly, the distribution of Ls-TPT and Ls-Gd was correlated very closely, and was not noticeably affected by the drug:lipid ratio of the Ls-TPT formulation. This seems to suggest that the liposomal carrier, independent of its drug load, determines the distribution characteristics of the compound.

The distribution of Ls-TPT and Ls-Gd in tumor tissue was correlated as closely as in naïve brain tissue, but the actual distribution volumes and corresponding Vd:Vi ratios were markedly smaller. This may in part be explained by alteration of CED kinetics due to intratumoral pressure and microanatomy of tumor tissue. However, the distribution of both Ls-TPT and Ls-GD in naïve brain tissue of the non-implanted hemisphere of tumor bearing rats was also impaired as compared to tumor-free animals. Therefore, it is proposed that increased intracranial pressure with tissue compression due to excessive tumor growth may be the most important factor underlying the reduced drug distribution in both tumor tissue and naïve brain tissue of tumor-implanted animals. This is supported by findings of massive tumor growth with hemispheric enlargement ipsilateral to the tumor xenograft and tumor protrusion through the cannula track with mass effects in a previous study (see Example 4).

In general, drug distribution was more variable in the tumor tissue groups than in the naïve brain tissue groups. Again, this may be explained with altered fluid dynamics associated with increased intracranial pressure. Minor distribution differences between the two Ls-TPT formulations in tumor-implanted animals were inconsistent (Vd values with D:L 0.1:1 nominally higher than with D:L 0.3:1 in naïve brain tissue, but nominally lower in tumor tissue) and mirrored by very similar differences that were observed for Ls-GD between the two tumor-tissue groups. This makes it unlikely that the differences were related to the liposomal formulation.

Lack of or minimal fluorescence in either naïve brain or tumor tissue of three animals was likely due to pump malfunction or leakage of the infusate into the subarachnoid space by suboptimal positioning of the cannula.

Example 6.4

Conclusions

The study demonstrated that CED of Ls-TPT and Ls-GD led to reliable and consistent drug distribution in both naïve rat brain and tumor tissue. CED fluid dynamics appear to be impacted by intracranial pressure, with high intracranial pressure due to excessive tumor growth leading to impaired drug distribution. There were no relevant differences between the two formulations of Ls-TPT tested (D:L 0.1:1 and D:L 0.3:1), and both formulations co-convected excellently with co-administered Ls-GD, confirming the suitability of Ls-GD as a liposomal tracer of Ls-TPT drug distribution following CED.

Example 7

Pilot Toxicology Assessment of Liposomal Topotecan and Liposomal Gadodiamide Administered by Intracerebral Convection-Enhanced Delivery to the Adult Athymic Rat

Example 7.1

Materials and Methods

Example 7.1.1

Test Articles

GLP grade material of both Ls-TPT and Ls-GD were prepared as described in Example 6.1.1.

Example 7.1.2

Animals and Grouping

Adult male athymic rats (rnu/rnu) (Taconic, Germantown, N.Y.) (batch 061207) weighing 200-270 g were used. The animals were divided in 2 groups based on nanoliposomal topotecan concentrations as outlined in Table 19.

TABLE 19

| Group Assignments and Dosing | | | | | | |
|---|---|---|---|---|---|---|
| Group | Ls-TPT concentration (µg/µL) | Ls-GD concentration (µg/µL) | Injection volume per hemisphere (µL) | Treatment time points | Sacrifice time points | Total number of animals to be used |
| 1 | 1.0 | 1.15 | 20 | Day 1 and 4 | Day 11 | 3 |
| 2 | 1.6 | 1.15 | 20 | Day 1 and 4 | Day 11 | 3 |
| | | | | | Total animals | 6 |

Ls-TPT = liposomal topotecan
Ls-GD = liposomal gadodiamide

Rats were assigned to groups based on body weight in a manner to achieve comparable group mean body weights and standard deviations.

Example 7.1.3

Surgical Procedures

On Day 1 and 4 of the study rats were to receive the test articles administered stereotactically into the striatum of each hemisphere using CED. The same coordinates were used for both treatments in this repeat dosing regimen. Rats were dosed in a systematic order that distributed the time of dosing similarly across both groups. Rats were anesthetized with either isoflurane (5% for induction; 2.5 to 3.0% for maintenance during surgery) inhalation or a combination of ketamine (90 mg/kg) and xylazine (12 mg/kg) via an intraperitoneal injection. The skin over the cranium was shaved and the animal mounted in a stereotaxic frame with the head positioned by the use of ear bars and the incisor bar. Aseptic techniques were used for all surgical procedures. The skin was disinfected with 70% alcohol followed by betadine solution. A longitudinal incision was made in the skin on top of the skull and blunt dissection was used to remove connective tissue overlying the skull. Craniectomy was performed using a small electric dental drill with two 1-mm diameter burr holes, 0.5 mm anterior and 3.0 mm left and right from the bregma. A fused silica cannula (OD 168 µm, ID 102 µm) (PolyMicro Technologies, Phoenix, Ariz.) connected to an automated pump (BASi, Inc., West Lafayette, Ind.) was used for CED in each hemisphere and was lowered to the appropriate dorso-ventral coordinates (−4.5 to −5 mm with the tooth bar at −3.3 mm). Dorso-ventral coordinates were calculated from the pial surface. The cannula was inserted into a 27-gauge needle and secured with superglue on the tubing. The test articles were administered bilaterally at one site into each striatum. A progressive infusion rate increment was used. The infusion rates to be used to administer the 20 µL volume per hemisphere were 0.2 µL/min for 15 min, 0.5 µL/min for 10 min and 0.8 µL/min for 15 min. Following infusion completion the cannula was left in place for 5 minutes to minimize outflow of infusate, and then slowly withdrawn.

Following completion of the procedure, the rats were maintained in a draft free environment, and kept warm via heating lamp or water bottle or other appropriate warming methods and monitored during anesthesia recovery. Buprenorphine was administered subcutaneously on an as needed basis. Rats were allowed to recover in the procedure room prior to returning to their home cages.

Example 7.1.4

Tissue Collection and Processing

Euthanasia was to take place on Day 11. Animals were anesthetized with isoflurane (2.5%) or CO2 inhalation. The animals were to have a transcardiac blood sample taken for the determination of topotecan plasma levels and other tests as appropriate. Subsequently, the animals were to undergo transcardiac perfusion with 100 mL heparinized saline followed by 300 mL 4% paraformaldehyde, and necropsied immediately.

A complete gross necropsy of all animals found dead or sacrificed (scheduled and unscheduled) during the study was performed on the carcass and muscular/skeletal system, all external surfaces and orifices, cranial cavity and external surface of the brain, neck with associated organs and tissues, thoracic, abdominal and pelvic cavities with their associated organs and tissues.

The brains were removed, equilibrated in 30% sucrose and subsequently frozen at 60° C. in a mixture of dry ice and isopentane. Brains were stored at 70° C. for subsequent processing. The heart, lungs, liver, kidneys, spleen (or portions of), when present, from any animal that died or was sacrificed, were collected and preserved. All of these tissues were fixed in neutral-buffered 10% formalin.

Formalin fixed organs were processed to paraffin blocks for subsequent histopathological analysis if required. All brains from each of the 2 groups in the study were sectioned with a 30 μm thickness and floating sections collected in phosphate buffered saline (PBS) and sodium azide 0.2%. Every fourth section was collected onto glass slides, fixed in 4% paraformaldehyde and processed for hematoxylin/eosin staining. Remaining sections were stored at 4° C. and could be used for additional immunohistochemical analyses.

Blood samples for plasma topotecan and gadodiamide extraction and measurement were centrifuged to separate plasma. Four-hundred μL of plasma per animal were obtained. Cold methanol 1.6 mL in 2.0 mL Eppendorf tubes was kept on ice and plasma was added to the tubes and then vortexed. The samples were to remain on ice until all the animals at the time point were processed. The tubes were sealed with parafilm to prevent the tops from opening accidentally and were stored frozen. Samples were shipped to Northern Lipids Inc. (Burbany, BC, Canada) on dry ice. The topotecan plasma levels were determined by high performance liquid chromatography (HPLC) with fluorescence detection and gadodiamide plasma levels by inductively coupled plasma mass spectroscopy (ICP-MS).

Example 7.1.5

Early Death/Unscheduled Sacrifice

If an animal died on study, the time of death was estimated as closely as possible and recorded, and necropsy was performed as soon as possible. If the necropsy could not be performed immediately, the animal was refrigerated (not frozen) to minimize tissue autolysis. The necropsy was performed no later than 12 hours after death.

If an animal appeared in poor condition or in extremis, it could be euthanized. If possible, blood or other specimens were collected and analyzed as appropriate (e.g., for clinical pathology parameters) to help reveal the cause of malaise/morbidity.

Example 7.1.6

Animal Care

Each animal was identified by a numbered ear tag and by cage cards specifying the animal identification number, study number, species/strain, sex, date of birth, source, and arrival date.

The animals were housed individually in isolator cages. The bedding material was shaved hardwood chips (Sanichips, Harlan, Calif.) and was changed weekly. Room temperature was centrally maintained at 18-26° C. (64-79° F.), with relative humidity at 30-70%. Temperature and humidity were continuously monitored and daily minimums and maximums recorded. A 12-hour light/12-hour dark cycle illumination period was maintained, except when room lights had to be turned on (during the dark cycle) to accommodate study procedures. The rats were to have ad libitum access to irradiated Teklad Global 18% Protein Rodent Diet (Harlan, San Diego, Calif., USA) and municipal tap water throughout the study period. No contaminants were known to be present in the diet or water at levels that would have a deleterious effect on the results of the study. Records of annual water quality testing are maintained in the PSI archives.

Upon arrival at the designated housing, all rats accepted for receipt following an initial health inspection were allowed to acclimatize to the housing environment (primary enclosure and room) for a minimum of 3 days prior to initiating any animal-related study procedures. During the acclimatization period, the general health of the rats was monitored daily. Only rats that were visually appraised to be in good clinical condition (i.e., within body weight specifications) were enrolled in the study. Any rats that appeared abnormal and exhibited signs of poor health (i.e., ruffled coat, significantly low body weight) were excluded from the study.

Clinical observations and measurements were performed at least once daily throughout the acclimation and study period. Recording of cage side observations were to commence at least 3 days prior to the first dose and were to continue until termination. Each animal was observed for changes in general appearance and behavior. Rats were weighed and body weights recorded the day after arrival, prior to test article administration, and the day of necropsy.

Example 7.2

Results

Example 7.2.1

Clinical Observations and Measurements

No animals had to be replaced in this study. No animals were found dead and all had scheduled sacrifice performed. The pre-sacrifice examination was normal in all animals.

Example 7.2.2

Topotecan Plasma Level Measurements

Plasma extract measurements at Day 11 (7 days after the last treatment) revealed both topotecan (lactone form only detected) and gadodiamide levels were either absent or below the lower limit of quantification as shown in Table 20. Topotecan carboxylate form was not observed or it was very low and overlapped with interfering peaks from the plasma. A peak at the retention time of topotecan lactone form was observed for each sample with the highest peak found in animal number 7214. Whether this peak was topotecan or from plasma blank could not be determined.

TABLE 20

Plasma Topotecan and Gadodiamide Levels in Plasma Extract

| Animal Study Number | Treatment Assignment | Topotecan (µg/mL) | Gadodiamide (µg/mL) |
|---|---|---|---|
| 7201 | Group 1 | <0.0007 | <0.04 |
| 7203 | Group 1 | <0.0007 | <0.04 |
| 7205 | Group 1 | <0.0007 | <0.04 |
| 7207 | Group 2 | <0.0007 | <0.04 |
| 7211 | Group 2 | <0.0007 | <0.04 |
| 7214 | Group 2 | <0.0007 | <0.04 |

Example 7.3

Discussion

This study evaluated the safety and toxicity of 2 concentrations of Ls-TPT co-infused with a fixed concentration of Ls-GD in rat normal brain tissue delivered via intracerebral CED. The concentrations of 1.0 and 1.6 mg/mL of Ls-TPT were intermediate between the safe (0.5 mg/mL) and toxic (5.0 mg/mL) Ls TPT concentrations established previously.

Both concentrations appeared equally safe with no gross or microscopic changes attributed to the test article. Areas of acute hemorrhage were mostly localized along the cannula tract and were presumably related to the experimental procedure and drug delivery system. Gross and microscopic changes related to the delivery technique including cannula insertion and CED have been described previously and the changes observed in this study are consistent with the delivery technique employed (Lieberman 1995, Lonser 2002). A no observable adverse effect level (NOAEL) was not established in this study as none of the concentrations evaluated resulted in toxicity attributable to the test article.

Plasma extract measurements 7 days after the last treatment revealed that both topotecan and gadodiamide levels were either absent or below the lower limit of quantification. A minute peak at the retention time of topotecan lactone form which was present in all samples could not clearly be attributed to topotecan or plasma. However, noticeable plasma levels would be somewhat unexpected given the loco-regional delivery method bypassing the blood brain barrier and the time between last treatment and sample collection. Brain tissue concentrations were not measured in this study because the brains were sectioned for histopathological analysis. It is therefore impossible to conclude whether the above peak in plasma was correlated with persisting brain parenchymal levels. In a separate study, no intracerebral topotecan was detected at 7 days after a single treatment with Ls-TPT in both hemispheres at a topotecan concentration of 0.5 µg/mL (Example 2).

Example 7.4

Conclusion

Ls-TPT at concentrations of 1.0 and 1.6 mg/mL co-infused with Ls-GD appears safe with no evidence of changes attributable to the test article in rat naïve brain tissue. Topotecan and gadodiamide plasma levels were below the lower level of quantitation for the assay consistent with the delivery method and drug properties.

Example 8

Convection-Enhanced Delivery of Liposomal Topotecan and Liposomal Gadodiamide to Intracranial Xenografted U87MG Tumors in the Adult Athymic Rat

Example 8.1

Materials and Methods

Example 8.1.1

Test Articles

GLP grade material of both Ls-TPT and Ls-GD were prepared as described in Example 6.1.1.

Example 8.1.2

Animals and Grouping

Adult male athymic rats rnu/rnu (Taconic, Germantown, N.Y., batch Apr. 30, 2007-150501) 6-8 weeks of age weighing 200-275 g were used. The animals were divided in 3 groups as outlined in Table 21.

TABLE 21

| | | | | | | | |
|---|---|---|---|---|---|---|---|
| | | | | Group Assignment and Dosing | | | |
| Group | Ls-TPT concentration (mg/mL) | Total dose (µg) | Injection volume per rat (µL) | Ls-GD concentration (mg/mL) | Treatment time points | Number of treatments (CED) | Sacrifice time points | Planned number of animals |
| 1 | 0.5 | 10 | 20 | 1.15 | Day 5, Day 8 | 2 | life span or Day 60 | 10 |
| 2 | 1.0 | 20 | 20 | 1.15 | Day 5, Day 8 | 2 | life span or Day 60 | 10 |

TABLE 21-continued

Group Assignment and Dosing

| Group | Ls-TPT concentration (mg/mL) | Total dose (µg) | Injection volume per rat (µL) | Ls-GD concentration (mg/mL) | Treatment time points | Number of treatments (CED) | Sacrifice time points | Planned number of animals |
|---|---|---|---|---|---|---|---|---|
| 3 | — | — | — | — | — | 0 | life span or Day 60 | 10 |
| Total | — | — | — | — | — | — | — | 30 |

Group 1: Ls-TPT 0.5 mg/mL + Ls-GD 1.15 mg/mL
Group 2: Ls-TPT 1.0 mg/mL + Ls-GD 1.15 mg/mL
Group 3: control (no treatment)
Ls-TPT = liposomal topotecan
Ls-GD = liposomal gadodiamide Tumor inoculation was performed over two days (n=15 rats/day). Five animals of each treatment group were inoculated with U87MG tumor cells on successive days The actual treatment allocation was to occur after tumor implantation on each of the two implantation days, aiming at comparable group mean body weights and standard deviations.

Example 8.1.3

Surgical Procedures and Treatment

Example 8.1.3.1

Intracranial Tumor Xenograft Implantation

Human glioblastoma cells (U87MG) were obtained from frozen cell stock (Perry Scientific Inc, San Diego, Calif.) two weeks prior to the scheduled inoculation. Cells were harvested on the day of tumor inoculation surgery and adjusted to a concentration of 50,000 to 100,000 cells/µL. On the day of inoculation (Day 0), each rat was implanted with a total of 500,000 U87MG tumor cells unilaterally into the right striatum using a 5-10 µL of suspension. A stereotaxic technique and anesthesia with isoflurane (2.5%) were used. The rat was mounted in a stereotaxic frame with the head positioned by the use of ear bars and the incisor bar. Aseptic techniques were used for all surgical procedures. The skin was disinfected with 70% alcohol followed by betadine solution. A longitudinal incision was made in the skin on top of the skull and blunt dissection was used to remove connective tissue overlying the skull. A burr hole was drilled 0.5 mm anterior and 3.0 mm lateral from the bregma. Using a 30 gauge 25 µL Hamilton syringe, U87MG cells were stereotaxically injected into the striatum using the appropriate dorso-ventral coordinates from pial surface (−4.5 to −5 mm with the tooth bar at −3.3 mm). Depending on the final cell concentration of the U87MG suspension, the volume of injection was adjusted between 5 and 10 µL to ensure that a total of 500,000±25,000 cells be delivered over a period of 10 minutes.

Following inoculation, the skin was stapled. The rats were monitored during anesthesia recovery. Buprenorphine was administered subcutaneously (SC) before the end of the procedure then buprenorphine was administered SC on an as needed basis. Rats were monitored twice daily following tumor cell implantation. The survival time following implantation was expected to be approximately 0-60 days, wherein the animal was euthanized and the brain harvested.

Example 8.1.3.2

Treatment

On both Day 5 and Day 8, active-treated rats (Groups 1 and 2) were to receive the test articles delivered to the intracerebral tumor by CED using the same coordinates that were used for the tumor implantation in the striatum. Control rats were to remain untreated and were not to undergo sham surgery. Rats were dosed in a systematic order that distributed the time of dosing similarly across all groups. Anesthesia was performed with either isoflurane (2.5%) or a combination of ketamine (90 mg/kg) and xylazine (12 mg/kg) via an intraperitoneal injection. A stereotaxic frame with blunt ear bars was used to perform CED through the previously performed burr hole. Only the blood clots were removed. A fused silica cannula (OD 168 µm, ID 102 µm) (PolyMicro Technologies, Phoenix, Ariz.) connected to an automated pump (BASi, Inc., West Lafayette, Ind.) was used for CED and was lowered to the dorso-ventral appropriate coordinates (−4.5 to −5 mm with the tooth bar at −3.3 mm). Dorso-ventral coordinates were calculated from the pial surface. The cannula was inserted into a 27-gauge needle and secured with superglue on the tubing. A progressive infusion rate increment was used. The infusion rates used in this study to achieve a 20 µL volume per treatment were 0.2 µL/min for 15 min, 0.5 µL/min for 10 min and 0.8 µL/min for 15 min. Following infusion the cannula was left in place for 5 minutes to avoid infusate outflow, and then slowly withdrawn.

Following completion of the procedure, the rats were maintained in a draft free environment, and kept warm via heating lamp or water bottle or other appropriate warming methods and monitored during anesthesia recovery. Buprenorphine was administered subcutaneously on an as needed basis. Rats were allowed to recover in the procedure room prior to return to their home cages.

Example 8.1.3.3

Euthanasia Criteria Before Day 60

If any one or a combination of symptoms (nasal/periorbital bleeding, paresis, hunching, inactivity or not feeding or grooming or weight loss >15% of baseline body weight) was observed, the animal could be euthanized. If possible, blood or other specimens were collected and analyzed as appropriate (e.g., for clinical pathology parameters) to help reveal the cause of malaise/morbidity. For euthanization, animals were be deeply anesthesized with isofluorane (2.5%) and then to undergo intracardiac perfusion with 0.9% saline (100 mL) followed by 4% paraformaldehyde (300 mL).

Example 8.1.3.4

Tissue Collection and Processing

A complete gross necropsy of all animals found dead or sacrificed (scheduled and unscheduled) during the study was performed on the carcass and muscular/skeletal system, all external surfaces and orifices, cranial cavity and external surface of the brain, neck with associated organs and tissues, thoracic, abdominal and pelvic cavities with their associated organs and tissues.

The brain was removed, incubated in 4% paraformaldehyde for up to 24 h, and then equilibrated in 30% sucrose. Following sucrose equilibration, the tissue was frozen and stored at −70° C. until cryosectioning. The heart, lungs, liver, kidneys, spleen (or portions of), when present, were also to be collected and preserved. These tissues were fixed in neutral-buffered 10% formalin. Formalin fixed organs were then to be grossed and processed to paraffin blocks for subsequent histopathological analyses if required.

Example 8.1.3.5

Histopathological Analyses

At least three randomly selected brains from both survivors and non-survivors at 60 days in each of the 3 treatment groups were sectioned with a 20 μm thickness and every fourth section was collected onto glass slides, fixed in 4% paraformaldehyde and processed for hematoxylin/eosin to assess the size and histology of the tumor mass. Remaining sections were stored at 4° C. and could be used for additional immunohistochemical analyses.

Example 8.1.3.6

In-Life Observations and Measurements

Clinical observations and measurements were performed at least once daily throughout the acclimation and study period. Recording of cage side observations were to commence at least 3 days prior to the first dose and were to continue until termination. Each animal was observed for changes in general appearance and behavior. The clinical observations and measurements are outlined in Table 22.

TABLE 22

Clinical Observations and Monitoring Parameters

| Monitoring Parameters | Frequency |
|---|---|
| Activity | Twice daily Monday through Sunday |
| Excreta | Twice daily Monday through Sunday |
| Appearance | Twice daily Monday through Sunday |
| Grooming | Twice daily Monday through Sunday |
| Posture | Twice daily Monday through Sunday |
| Weight | Twice weekly (following intracranial tumor implantation) and one terminal body weight prior to necropsy |
| Food Consumption | Weekly |
| Behavior | Twice daily Monday through Sunday |

Example 8.1.3.7

Early Death/Unscheduled Sacrifice

If an animal died on study, the time of death was estimated as closely as possible and recorded, and necropsy was performed as soon as possible. If the necropsy could not be performed immediately, the animal was refrigerated (not frozen) to minimize tissue autolysis. The necropsy should be performed no later than 12 hours after death.

If an animal appeared in poor condition or in extremis, it could be euthanized. If possible, blood or other specimens were collected and analyzed as appropriate (e.g., for clinical pathology parameters) to help reveal the cause of malaise/morbidity.

Example 8.1.3.8

Statistical Methods

For survival analysis purposes animals were grouped by treatment arm. A Kaplan-Meier survival analysis was performed using a log rank statistic for comparative purposes. Median survival times were presented based on the KM curve. Separate analyses of survival were performed with euthanized animals considered as either uncensored (dead) and censored (alive).

Example 8.1.4

Animal Care

Each animal was identified by a numbered ear tag. Additionally, each animal's cage was identified by a cage card listing the animal identification number, study number, group, source, arrival date, species/strain, date of birth and sex of the animal.

The animals were housed individually in isolator cages. The bedding material was shaved hardwood chips (Sanichips, Harlan, Calif.) and was changed weekly. Room temperature was centrally maintained at 18-26° C. (64-79° F.), with relative humidity at 30-70%. Temperature and humidity were continuously monitored and daily minimums and maximums recorded. A 12-hour light/12-hour dark cycle illumination period was maintained, except when room lights had to be turned on (during the dark cycle) to accommodate study procedures.

The rats were to have ad libitum access to irradiated Teklad Global 18% Protein Rodent Diet (Harlan, San Diego, Calif., USA) and municipal tap water throughout the study period. No contaminants were known to be present in the diet or water at levels that would have a deleterious effect on the results of the study. Records of annual water quality testing are maintained in the PSI archives.

Upon arrival at the designated housing, all rats accepted for receipt following an initial health inspection were allowed to acclimatize to the housing environment (primary enclosure and room) for a minimum of 3 days prior to initiating any animal-related study procedures. During the acclimatization period, the general health of the rats was monitored daily. Only rats that were visually appraised to be in good clinical condition (i.e., within body weight specifications) were enrolled in the study. Any rats that appeared abnormal and exhibited signs of poor health (i.e., ruffled coat, significantly low body weight) were excluded from the study.

Example 8.2

Results

Example 8.2.1

Clinical Observations and Measurements

No animals had to be replaced. Eight animals were found dead in their cage (5 in group 1, one in group 2 and 3 in group 3). Twenty-one animals had to be euthanized (5 in group 1, 9 in group 2 and 7 in group 3) because they appeared in poor conditions, the most common signs being weight loss ≥15%, lethargy, hunched back posture, and motor deficit (e.g. altered righting reflex, laying on one side).

Example 8.2.2

Efficacy

Figure 12:
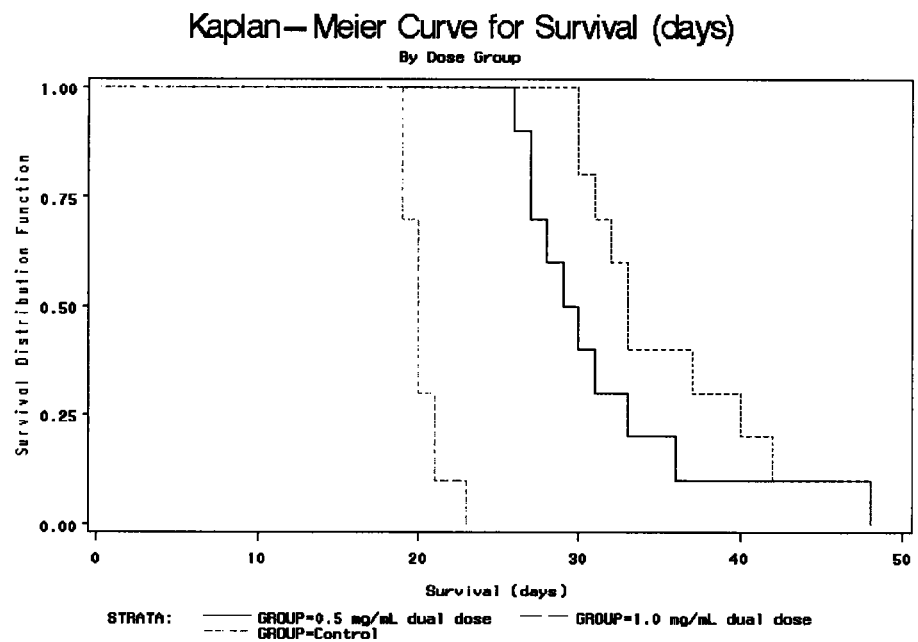
FIG. 12 shows survival of animals by treatment groups (euthanized animals considered as uncensored).

Ten animals were treated in each group as planned. The main efficacy analysis considered euthanized animals as uncensored (dead). Consequently the survival times shown represent time to death. Individual survival for each animal as well as median and mean survival by treatment group are shown in Table 23. Survival curves by treatment group are presented in FIG. 12.

TABLE 23

Individual, Treatment Group, and Overall Survival* with Euthanized Animals Considered as Uncensored

| Group | Total number of animals | Individual survival (days) | Median survival (days) | Mean Survival (days) |
| --- | --- | --- | --- | --- |
| 1 | 10 | 26 d, 27 d, 27 d, 28 d, 29 d, 30 d, 31 d, 33 d, 36 d, 48 d | 29.5 (95% CI, 27.0-33.0) | 31.5 |
| 2 | 10 | 30 d, 30 d, 31 d, 32 d, 33 d, 33 d, 37 d, 40 d, 42 d, 48 d | 33.0 (95% CI, 31.0-40.0) | 35.6 |
| 1 and 2 combined | 20 | — | 31.5 (95% CI, 30.0-36.0) | 33.5 |
| 3 | 10 | 19 d, 19 d, 19 d, 20 d, 20 d, 20 d, 20 d, 21 d, 21 d, 23 d | 20.0 (95% CI, 19.0-21.0) | 20.2 |
| Overall | 30 | — | 29.5 | 29.1 |

*Time to death
Group 1: Ls-TPT 0.5 mg/mL + Ls-GD 1.15 mg/mL (Day 5 and Day 8)
Group 2: Ls-TPT 1.0 mg/mL + Ls-GD 1.15 mg/mL (Day 5 and Day 8)
Group 3: control (no treatment)
Ls-TPT = liposomal topotecan
Ls-GD = liposomal gadodiamide The data reveal a longer survival for animals treated in group 2 at the higher topotecan total dose and concentration but also in group 1 at the lower topotecan total dose and concentration compared to controls (group 3) with median survivals of 33.0 (95% CI, 31-40), 29.5 (95% CI, 27-33) and 20.0 (95% CI, 19-21) days, respectively. These differences were all statistically significant when compared to control (1.0 mg/mL vs. controls, p<0.0001 and 0.5 mg/mL vs. controls, p<0.0001). Median survival for the actively treated groups combined (groups 1 and 2) was 31.5 (95% CI, 30-36) days and also statistically significant when compared to controls, p<0.0001. Although a dose/concentration response trend is observed with a hazard ratio of 0.567 (95% CI, 0.23-1.38), the difference between the two actively treated groups does not reach the level of statistical significance (0.5 mg/mL vs 1.0 mg/mL, p=0.215).

Figure 13:
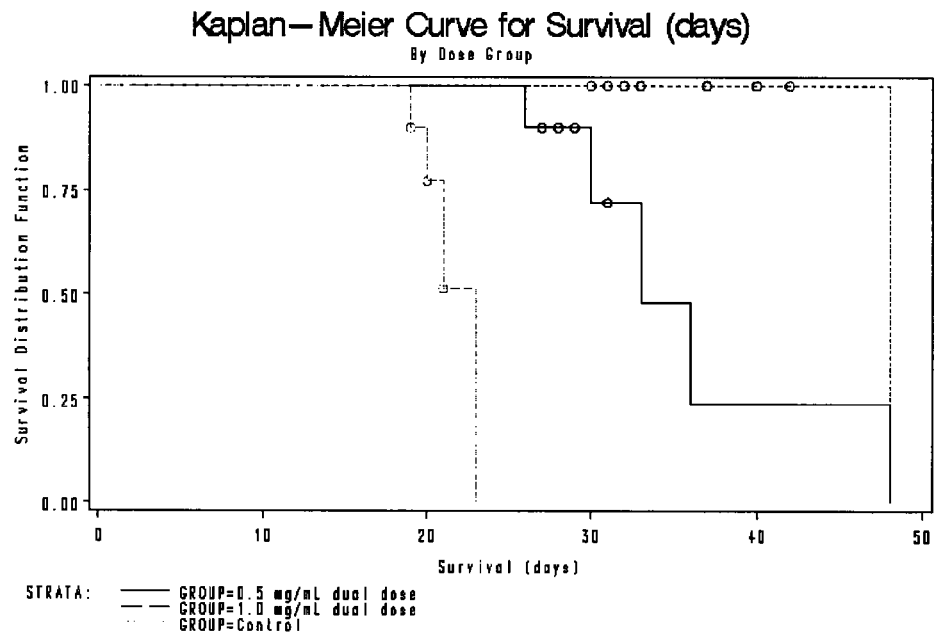
FIG. 13 shows survival of animals by treatment groups (euthanized animals considered as censored.

A secondary efficacy analysis was performed considering euthanized animals as censored. Median survival by treatment group is shown in Table 24, and survival curves by treatment group are presented in FIG. 13.

TABLE 24

Treatment Group and Overall Survival with Euthanized Animals Considered as Censored

| Group | Total number of animals | Number of animals euthanized | Median survival (days) |
| --- | --- | --- | --- |
| 1 | 10 | 5 | 33.0 (95% CI, 30.0-48.0) |
| 2 | 10 | 9 | 48.0 (N/D) |
| 1 and 2 combined | 20 | 14 | 48.0 (95% CI, 36.0-48.0) |
| 3 | 10 | 6 | 23.0 (95% CI, 20.0-23.0) |
| Total | 30 | 20 | ? |

Group 1: Ls-TPT 0.5 mg/mL + Ls-GD 1.15 mg/mL (Day 5 and Day 8)
Group 2: Ls-TPT 1.0 mg/mL + Ls-GD 1.15 mg/mL (Day 5 and Day 8)
Group 3: control (no treatment)
Ls-TPT = liposomal topotecan
Ls-GD = liposomal gadodiamide
N/D = not determined This analysis is consistent with and supports the one considering euthanized animals as uncensored, revealing a longer survival for animals treated in group 2 at the higher topotecan total dose and concentration but also in group 1 at the lower topotecan total dose and concentration compared to controls (group 3) with median survivals of 48.0 (95% CI, not determined), 33.0 (95% CI, 30.0-48.0) and 23.0 (95% CI, 20.0-23.0) days, respectively. These differences were also statistically significant when compared to control (1.0 mg/mL vs. controls, p=0.0014 and 0.5 mg/mL vs. controls, p=0.0014). Median survival for the actively treated groups combined (group 1 and 2) was 48.0 (95% CI, 36.0-48.0) days and also statistically significant when compared to controls, p<0.0001.

This confirmatory efficacy study evaluated the efficacy of a combined drug delivery approach using a novel liposomal topotecan formulation at two concentrations delivered to an intracranial glioma xenograft model in athymic rats by intracerebral CED. Liposomes loaded with gadodiamide were co-administered as potential imaging tracer surrogate for liposomal topotecan. The topotecan concentrations selected for the study included 0.5 mg/mL which was tested in a preceding exploratory efficacy study (Example 4), and 1.0 mg/mL which was well within the non-toxic range as defined in a preceding pilot toxicology study (Example 7). Based on the findings of the Example 4, a dual dosing strategy was used in this study, and the start of treatment after tumor xenograft implantation was moved up to Day 5 (vs Day 8 in Example 4) in order to avoid excessive tumor burden and consequently optimize tumor coverage by the volume of distribution. Also, the U87MG tumor cell load at xenograft implantation was kept similar across all groups at $5 \times 10^5$ tumor cells in order to obtain a similar tumor burden for all animals (the tumor cell load varied from 6.8 to $9.7 \times 10^5$ in the study disclosed in Example 4).

Longer overall and median survivals were observed for both active treated groups. As compared to controls, the higher Ls-TPT concentration (1.0 mg/mL) resulted in a highly statistically significant increase in overall survival ($p<0.0001$), with a 65% and 76% increase in median and mean survival, respectively. The lower Ls-TPT concentration (0.5 mg/mL) also produced a highly statistically significant increase in overall survival when compared to controls ($p<0.0001$), but the effect size was slightly more moderate than with the higher Ls-TPT concentration and thus, suggestive of a dose/concentration dependent effect. The increase in median and mean survival relative to controls was 48% and 56%, respectively, with the lower Ls-TPT concentration. Similar findings were observed when the survival analysis was performed with euthanized animals considered as censored which is a more conservative assessment method preventing any potential overestimation of the true effect size of Ls-TPT while possibly underestimating that effect. The results of that secondary efficacy analysis were still statistically significant and strongly support the primary efficacy analysis findings in which euthanized animals are considered as uncensored.

The overall findings of the experiments described in this confirmatory efficacy study differ from those reported in study disclosed in Example 4. The longer median and overall survivals observed for animals receiving Ls-TPT at concentrations of 0.5 or 1.0 mg/mL are consistent with the use of a slightly lower and constant tumor cell load at xenograft implantation, earlier treatment timing after tumor xenograft implantation and dual treatment (Day 5 and 8). The importance of the tumor cell load for survival is indicated by the longer median survival of control animals in this study (20 days) which was very similar to the one reported by Saito et al. (Saito 2006) and longer than in the study disclosed in Example 4 (17 days).

Example 8.4

Conclusion

Ls-TPT administered by CED in a rat glioma model using U87MG results in a clear and consistent survival advantage as compared to untreated controls.

Example 9

Convection-Enhanced Delivery of Liposomal ω-Conotoxin to Kindled Rats

Synthetic ω-CTX-G (27 amino acids; MW, 3037), ω-CTX-M (25 amino acids; MW, 2639), and carbamazepine are obtained from Sigma-Aldrich (St. Louis, Mo.). Each is loaded into liposomes composed of distearoylphosphatidylcholine (DSPC), distearoylphosphatidylglycerol (DSPG), and cholesterol (see, e.g., Example 2.1.2). The effects of liposomal ω-CTX-G, liposomal ω-CTX-M, native ω-CTX-G, native ω-CTX-M, and native carbamazepine on kindled rats are determined using convection enhanced delivery and a protocol substantially similar to that described in Gasior et al. (2007) J. Pharmacology and Experimental Therapeutics 323: 458-68.

Briefly, a cannula-bipolar stimulating electrode assembly is chronically implanted into each rat such that the electrode tip is placed into the basolateral nucleus of the right amygdala at stereotaxic coordinates (AP: −2.8 mm; ML: 5.0 mm; DV: −8.7 mm) measured from bregma (Paxinos G and Watson C (1998) The rat brain in stereotaxic coordinates, 4th ed. Academic Press, Sydney). Dental acrylic cement (Lang Dental, Wheeling, Ill.) and stabilizing stainless steel screws (Plastics One) are used to secure the cannula-electrode assembly to the skull and at least ten days are allowed for recovery after the surgery. Kindling consists of three phases: (1) pre-kindling determination of the AD threshold; (2) kindling development, and (3) post-kindling redetermination of the AD threshold (Pinel, J. P., et al. (1976) Epilepsia 17:197-206; Freeman, F. G. and Jarvis, M. F. (1981) Brain Res. Bull. 7:629-33; Gasior et al. (2007) J. Pharmacology and Experimental Therapeutics 323:458-68). During kindling, rats are stimulated individually within a 29 cm diameter Plexiglas cylinder with a custom made stimulator (National Institutes of Health Research Services Branch, Bethesda, Md.) via a swivel attachment to allow free movement within the chamber.

The convection enhanced delivery system is substantially described in Gasior et al. (2007), supra). For convection enhanced delivery, each rat is restrained and the infusion cannula is slowly inserted into the brain through the guide cannula. The tip of the infusion cannula extends to a depth 0.5 mm above the tips of the stimulating electrode wires and is maintained at the appropriate depth by a plastic stop at the top of the cannula. The rat is released and placed in a plastic cylinder for the entire infusion. All infusions are performed in conscious and unrestrained animals. After infusion cannula insertion, the brain tissue is allowed to seal around the cannula for a few minutes before initiation of the infusion. A progressive infusion rate increment is used. The infusion rates used to administer 20 μL volume per hemisphere are 0.2 μL/min for 15 min, 0.5 μL/min for 10 min, and 0.8 μL/min for 15 min. Following infusion completion, the cannula is left in place for 5 min to minimize the outflow of infusate and then slowly withdrawn. The effects of test substances on seizure sensitivity in fully-kindled rats are assessed by establishing the AD threshold and measuring the AD duration, seizure stage and behavioral seizure duration. Following CED infusion of the test substances, animals are stimulated and kindling measures are determined 20 min post-infusion as well as on the subsequent days at 24 h, 48 h, 72 h, 96 h, 1 week, 2 weeks, 4 weeks, and 8 weeks post-infusion. Each rat is observed for the occurrence of tremor (rhythmic oscillatory movements of the limbs, head and trunk) or other neurological signs during the test substance infusion, for at least 1 hour after the infusion, and before each subsequent stimulation session.

At the end of the studies characterizing toxin effects on kindling measures, fully-kindled rats are randomly selected for the locomotor activity testing with a VersaMax Animal Activity Monitoring System (AccuScan Instruments, Columbus, Ohio). Briefly, each rat is exposed to a locomotor-activity chamber (Gasior et al. (2007), supra) for 60 min on 5 successive days to allow habituation. Horizontal and vertical activity trends toward a stable baseline over the 5-day period; the means of the activity counts during the test session on the final two days of the habituation period are taken as the baseline for the infusion studies. On the day after the completion of the 5-day habituation period, each rat receives an infusion of a test substance. The parameters of the infusion and other factors including animal handling and external cues are identical to those in the kindled seizure experiments. Horizontal and vertical beam interruptions are determined in 60 min periods beginning 20 min post infusion and on subsequent days at 24 h, 48 h, 72 h 96 h, 1 week, 2 weeks, 4 weeks, and 8 weeks post infusion.

After the completion of testing, selected animals are perfused transcardially with 4% paraformaldehyde and the brains are removed for sectioning and cresyl violet and silver staining to assess cannula placement and evidence of neuronal damage. The effects of each drug treatment are expressed as a change (in percent) from baseline calculated using the following formula: 100×[(value before treatment)−(value after treatment)]/(value before treatment). Treatment effects with respect to baseline for each rat are calculated separately and then averaged for a group. Statistical analyses of the data from the kindling and locomotor-activity testing are performed by one-way (within a group) and two-way (between groups) repeated measures analysis of variance (ANOVA) after transformation of the percentage change data using arcsine-root transformation. When appropriate, post hoc analysis is performed using Dunnett's test or Tukey's test. Tremor data are expressed as frequencies analyzed by the Fisher's exact probability test.

REFERENCES

1. Stupp R, Mason W P, van den Bent M J et al. Radiotherapy plus concomitant and adjuvant temozolomide for glioblastoma. N Engl J Med 352:987-996, 2005
2. Bobo R H, Laske D W, Akbasak A, et al. Convection-enhanced delivery of macromolecules in the brain. Proc Natl Acad Sci USA 91:2076-2080, 1994
3. Lieberman D M, Laske D W, Morrison P F, et al. Convection-enhanced distribution of large molecules in gray matter during interstitial drug infusion. J Neurosurg 82:1021-1029, 1995
4. Morrison P F, Laske D W, Bobo H, et al. High-flow microinfusion: tissue penetration and pharmacodynamics. Am J Physiol 266:R292-305, 1994
5. Croteau D, Walbridge S, Morrison P F, Butman J A, Vortmeyer A O et al. Real-time in vivo imaging of the convective distribution of a low-molecular-weight tracer. J Neurosurg 102: 90-97, 2005
6. Lonser R R, Walbridge S, Garmestani K, Butman J A, Walters H A et al. Succesful and safe perfusion of the primate brainstem: in vivo magnetic resonance imaging of macromolecular distribution during infusion. J Neurosurg 97:905-913, 2002
7. Sampson J H, Brady M L, Petry N A, Croteau, D, Friedman A H et al. Intracerebral infusate distribution by convection-enhanced delivery in humans with malignant gliomas: descriptive effects of target anatomy and catheter positioning. Neurosurgery 60 [ONS Suppl 1]:89-98, 2007
8. Moog R, Burger A M, Brandi M et al. Change in pharmacokinetics and pharmacodynamic behavior of gemcitabine in human tumor xenografts upon entrapment in vesicular phospholipid gels. Cancer Chemother Pharmacol 49:356-366, 2002
9. Saito R, Krauze M T, Noble C O, Drummond D C, Kirpotin D B et al. Convection-enhanced delivery of Ls-TPT enables an effective, continous, low-dose chemotherapy against malignant glioma xenograft model. Neuro-Oncol 8:205-214, 2006
10. Schmidt F, Rieger J, Wischhusen J, Naumann U, Weller M. Glioma cell sensitivity to topotecan: the role of p53 and topotecan-induced DNA damage. Eur J Pharmacology 412:21-25, 2001
11. Kaiser M G, Parsa A T, Fine R L, Hall J S, Chakrabarti I et al. Tissue distribution and antitumor activity of topotecan delivered by intracerebral clysis in a rat glioma model. Neurosurg 47: 1391-1398, 2000
12. Pollina J, Plunkett R J, Ciesielski M J, Lis A, Barone T A et al. Intratumoral infusion of topotecan prolongs survival in the nude rat intracranial U87 human glioma model. J Neuro-Onc 39:217-225, 1998
13. Lonser R R, Schiffman R, Robison R A, Butman J A, Quezado J et al. Image-guided, direct convective delivery of glucocerebrosidase for neuronopathic Gaucher disease. Neurology 68:254-261, 2007
14. Murad G J, Walbridge S, Morrison P F, Garmestani K, Degen J W et al. Real-time, image-guided, convection-enhanced delivery of interleukin 13 bound to pseudomonas exotoxin. Clin Cancer Res 12(10):3145-3151, 2006
15. Saito R, Bringas J R, McKnight T R, Wendland M F, Mamot C et al. Distribution of liposomes into brain and rat brain tumor models by convection-enhanced delivery monitored with magnetic resonance imaging. Cancer Res 64:2572-79, 2004
16. Saito R, Krauze M T, Bringas J R, Noble C, McKnight T R et al. Gadolinium-loaded liposomes allow for real-time magnetic resonance imaging of convection-enhanced delivery in the primate brain. Exp Neurol 196(2):381-389, 2005

All citations are expressly incorporated herein in their entirety by reference.

We claim:

1. A diagnostic composition comprising a non-PEGylated liposomal delivery vehicle for administering pharmaceutical agents via convection-enhanced delivery to the central nervous system, said vehicle comprising a diagnostic agent encapsulated in a liposomal formulation, wherein the ratio of said diagnostic agent to said liposomal formulation is between 0.3:1 and 0.5:1 (w/w), wherein said liposomal formulation consists essentially of DSPC, DSPG and CHOL at a 7:2:1 molar ratio, and wherein said liposomal formulation comprises liposomes having a mean diameter of between 75 and 120 nm.

2. The diagnostic composition according to claim 1, wherein said liposomal formulation encapsulates an MRI magnet.

3. The diagnostic composition according to claim 2, wherein the MRI magnet is selected from the group consisting of gadodiamide and rhodamine.

4. The diagnostic composition according to claim 1, wherein said liposomes have a mean diameter of between 100 and 120 nm.

5. A therapeutic composition comprising a non-PEGylated liposomal delivery vehicle for administering pharmaceutical agents via convection-enhanced delivery to the central nervous system, said vehicle comprising a therapeutic agent encapsulated in a liposomal formulation, wherein the ratio of said therapeutic agent to said liposomal formulation is between 0.3:1 and 0.5:1 (w/w), wherein said liposomal formulation consists essentially of DSPC, DSPG and CHOL at a 7:2:1 molar ratio, and wherein said liposomal formulation comprises liposomes having a mean diameter of between 75 and 120 nm.

6. The therapeutic composition according to claim 5, wherein said liposomes have a mean diameter of between 75 and 90 nm.

7. The therapeutic composition according to claim 5, wherein said liposomal formulation encapsulates a topoisomerase inhibitor.

8. The therapeutic composition according to claim 7, wherein said topoisomerase inhibitor is topotecan.

9. The therapeutic composition according to claim 7, wherein said topoisomerase inhibitor is present at an initial drug concentration of at least about 500 ug/mL.

10. The therapeutic composition according to claim 5, wherein said liposomal formulation encapsulates a toxin.

11. The therapeutic composition according to claim 10, wherein said toxin is selected from the group consisting of ω-conotoxin, botulinum toxin, μ-conotoxin and α-conantokin peptide.

12. The therapeutic composition according to claim 11, wherein said protein toxin is a conotoxin.

* * * * *